(12) United States Patent
Ohtani et al.

(10) Patent No.: US 11,106,769 B2
(45) Date of Patent: Aug. 31, 2021

(54) INFORMATION PROCESSING APPARATUS AND INFORMATION PROCESSING METHOD

(71) Applicant: SONY CORPORATION, Tokyo (JP)

(72) Inventors: Shinya Ohtani, Kanagawa (JP); Yuya Hirano, Tokyo (JP); Katsuyoshi Kanemoto, Chiba (JP)

(73) Assignee: SONY CORPORATION, Tokyo (JP)

( * ) Notice: Subject to any disclaimer, the term of this patent is extended or adjusted under 35 U.S.C. 154(b) by 125 days.

(21) Appl. No.: 15/560,214

(22) PCT Filed: Dec. 28, 2015

(86) PCT No.: PCT/JP2015/086549
§ 371 (c)(1),
(2) Date: Sep. 21, 2017

(87) PCT Pub. No.: WO2016/157663
PCT Pub. Date: Oct. 6, 2016

(65) Prior Publication Data
US 2018/0046788 A1 Feb. 15, 2018

(30) Foreign Application Priority Data

Mar. 31, 2015 (JP) .............................. JP2015-073744

(51) Int. Cl.
*G06F 21/31* (2013.01)
*G06F 3/01* (2006.01)
(Continued)

(52) U.S. Cl.
CPC .............. *G06F 21/316* (2013.01); *G06F 3/01* (2013.01); *G06F 21/32* (2013.01); *G06F 3/011* (2013.01); *G16H 20/30* (2018.01)

(58) Field of Classification Search
CPC .......... G06F 21/316; G06F 21/32; G06F 3/01; G06F 3/011
See application file for complete search history.

(56) References Cited

U.S. PATENT DOCUMENTS 7,242,952 B2 * 7/2007 Shirai ................. H04M 19/041
455/404.1
7,727,158 B2 6/2010 Kitajima et al.
(Continued)

FOREIGN PATENT DOCUMENTS

CN 103455789 A 12/2013
EP 2418603 A1 2/2012
(Continued)

OTHER PUBLICATIONS

Young-guk Ha et al.,"A Ubiquitous Homecare Service System Using a Wearable User Interface Device," 2012, pp. 649-650 (Year: 2012).*

(Continued)

*Primary Examiner* — Luu T Pham
*Assistant Examiner* — Canh Le
(74) *Attorney, Agent, or Firm* — Chip Law Group

(57) ABSTRACT

Provided is an information processing apparatus including a processing unit configured to perform a predetermined process on the basis of first information about a user that is acquired by a first apparatus from around a body of the user, and second information about a user that is acquired by a second apparatus different from the first apparatus.

11 Claims, 18 Drawing Sheets

(51) Int. Cl.
*G06F 21/32* (2013.01)
*G16H 20/30* (2018.01)

(56) References Cited

U.S. PATENT DOCUMENTS

| | | | | |
|---|---|---|---|---|
| 2005/0124463 | A1* | 6/2005 | Yeo | A63B 69/00 |
| | | | | 482/8 |
| 2005/0234312 | A1* | 10/2005 | Suzuki | A61B 5/681 |
| | | | | 600/300 |
| 2006/0258944 | A1* | 11/2006 | Takahashi | A61B 5/022 |
| | | | | 600/485 |
| 2011/0178931 | A1* | 7/2011 | Kia | G06Q 10/06 |
| | | | | 705/50 |
| 2012/0019379 | A1* | 1/2012 | Ben Ayed | G06F 21/32 |
| | | | | 340/539.1 |
| 2012/0030743 | A1 | 2/2012 | Semba | |
| 2014/0101710 | A1* | 4/2014 | Kim | H04N 21/235 |
| | | | | 725/110 |
| 2014/0156735 | A1* | 6/2014 | Yamasaki | G06F 9/5027 |
| | | | | 709/203 |
| 2015/0006534 | A1 | 1/2015 | Konoshima | |
| 2015/0010214 | A1* | 1/2015 | Ishizawa | G06T 7/73 |
| | | | | 382/106 |
| 2015/0161836 | A1* | 6/2015 | Park | B60R 25/2045 |
| | | | | 340/5.51 |

FOREIGN PATENT DOCUMENTS

| | | | |
|---|---|---|---|
| JP | 2003-331268 | A | 11/2003 |
| JP | 2005-005787 | A | 1/2005 |
| JP | 2005-258869 | A | 9/2005 |
| JP | 2006-283383 | A | 10/2006 |
| JP | 2007-184857 | A | 7/2007 |
| JP | 2014-211677 | A | 11/2014 |
| WO | 2010/116506 | A1 | 10/2010 |
| WO | 2013/136528 | A1 | 9/2013 |

OTHER PUBLICATIONS

Ranajit Chatterjee et al., "Design A Touch Sensor Based Single Finger Operated Wearable User-Interface Terminal," 2006, pp. 4142-4147. (Year: 2006).*

"Musen Naradewa no Kiki Sekkei Adhoc ni Tsunagu Tarinai Kino wa Karirebaii", Nikkei Electronics, Jun. 17, 2002, pp. 122-123.

Konno, et al., "A Study on Personal Authentication Method by Walking Motion Using Wearable Sensor", IEICE Technical Report, vol. 114, No. 480, Feb. 23, 2015, pp. 145-152.

Yuji Watanabe, "Comparison of Operational Features for Authentication Based on Touch Operation on Android Device", Computer Security Symposium 2014, vol. 2014, No. 2, Oct. 15, 2014, pp. 1015-1022.

"Ad hoc connection Need a function? Just borrow it!", Nikkei Electronics, Jun. 17, 2002, 6 pages.

Konno, et al., "A Study on Personal Authentication Method by Walking Motion Using Wearable Sensor", IPSJ SIG Technical Report, vol. 2015-MBL-74, No. 25, 2015, 11 pages.

Yuji Watanabe, "Comparison of operational features for authentication based on touch operation on Android device", Computer Security Symposium, Oct. 22-24, 2014, pp. 1015-1022.

International Search Report and Written Opinion of PCT Application No. PCT/JP2015/086549, dated Feb. 9, 2016, 10 pages of ISRWO.

"Future of Mobile Payment: Deep Integration with Wearable Devices", Wearable.ofweek.com, Nov. 20, 2014, 02 pages.

Office Action for CN Patent Application No. 201580078176.1, dated Jul. 3, 2020, 10 pages of Office Action and 17 pages of English Translation.

Extended European Search Report of EP Application No. 15887805.8, dated Jan. 25, 2021, 12 pages.

Office Action for CN Patent Application No. 201580078176.1, dated May 26, 2021, 04 pages of Office Action.

* cited by examiner

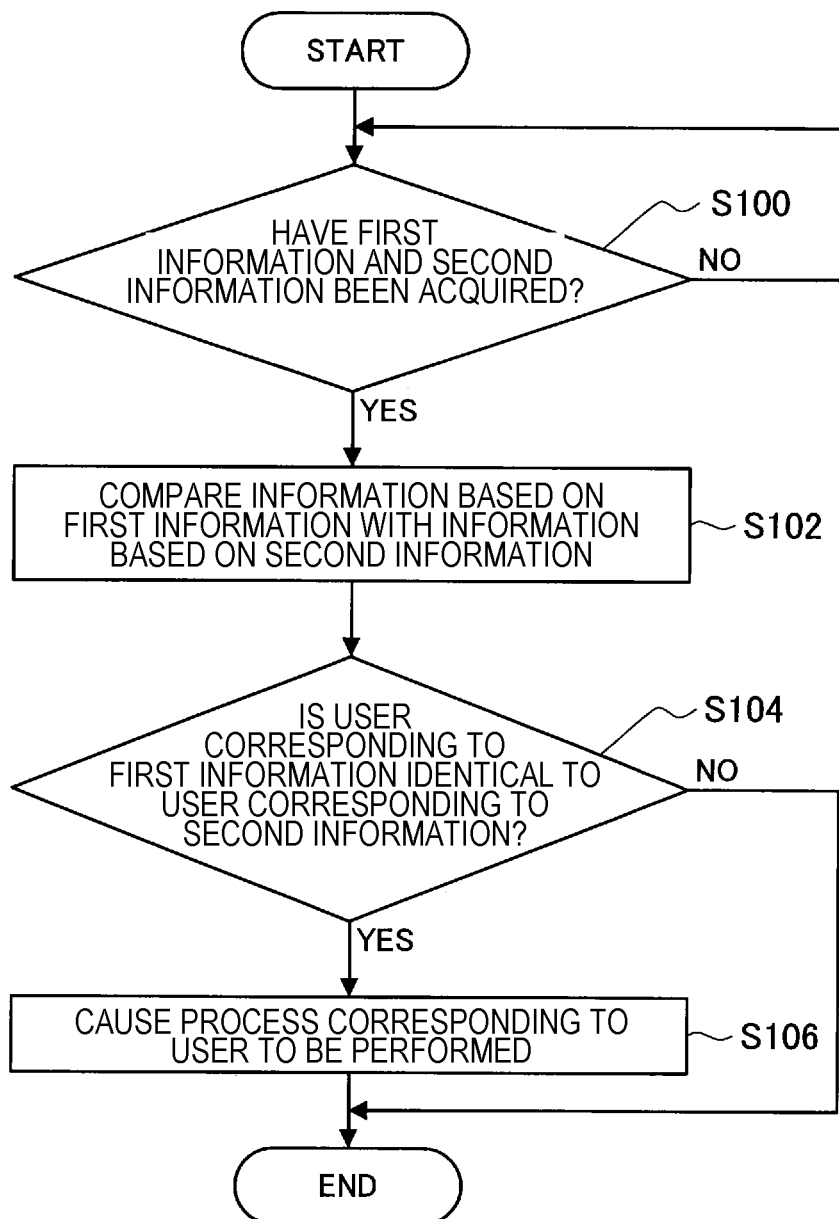

FIG. 3A

| ACCOUNT ID | OWNED DEVICE |
|---|---|
| X | A |
| Y | B |
| Z | C |
| ⋮ | ⋮ |

FIG. 3B

| DEVICE ID | INFORMATION ON OWNER | TIME OF INFORMATION |
|---|---|---|
| A | ○○ | 21:37 |
| B | △△ | 21:36 |
| C | □□ | 8:20 |
| ⋮ | ⋮ | ⋮ |

FIG. 3C

| ACCOUNT ID | AUTHORITY |
|---|---|
| X | Admin |
| Y | Operator |
| Z | Guest |
| ⋮ | ⋮ |

FIG. 7
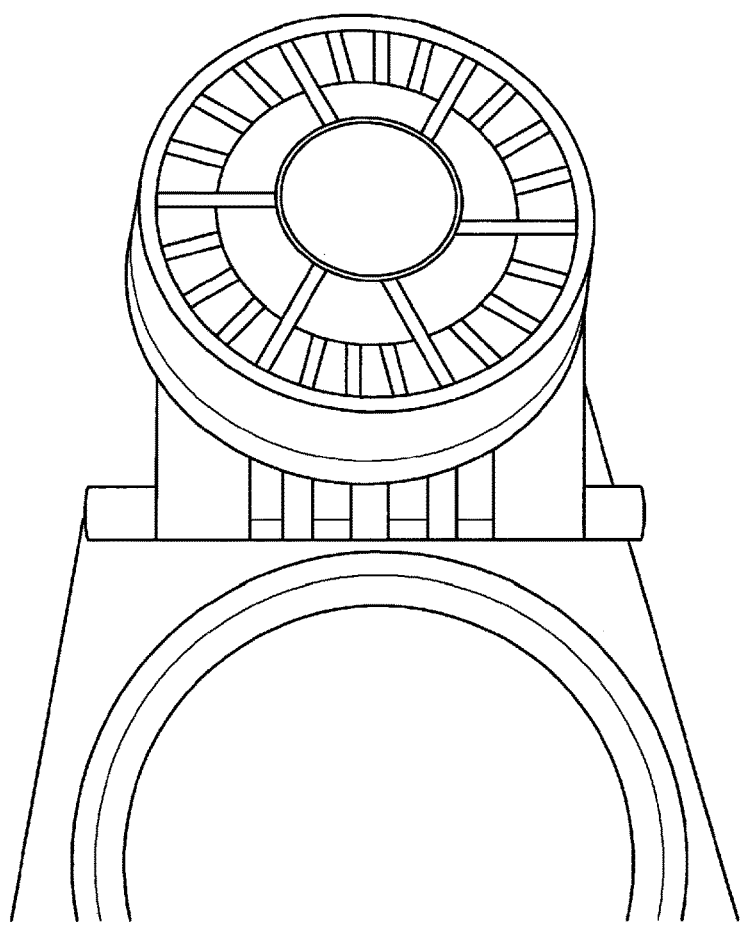

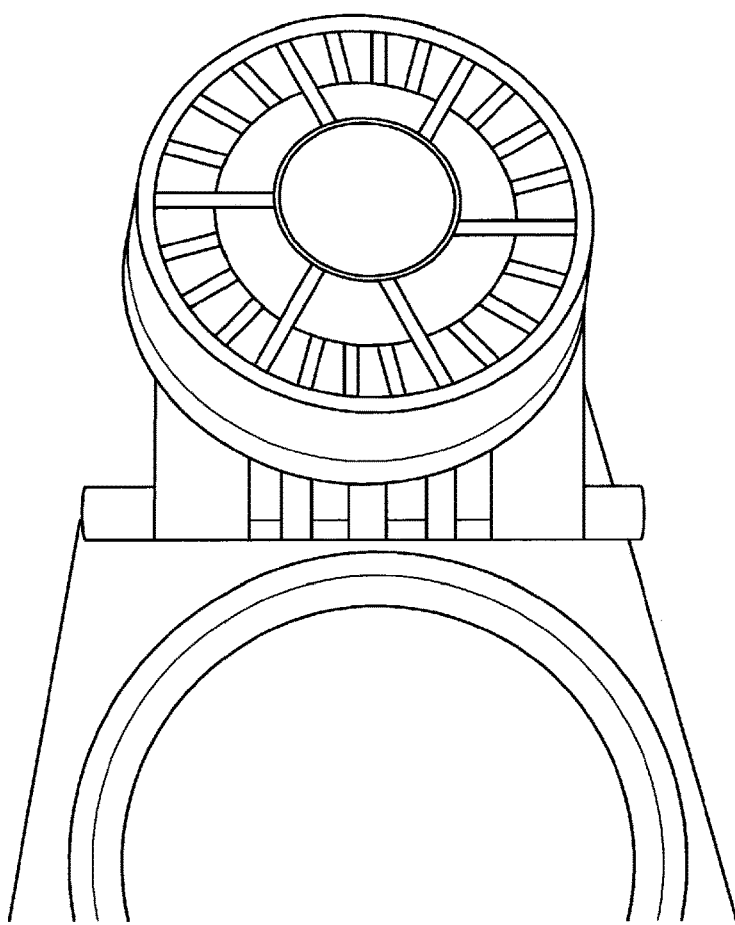
FIG. 9

FIG. 15A
FIG. 15B
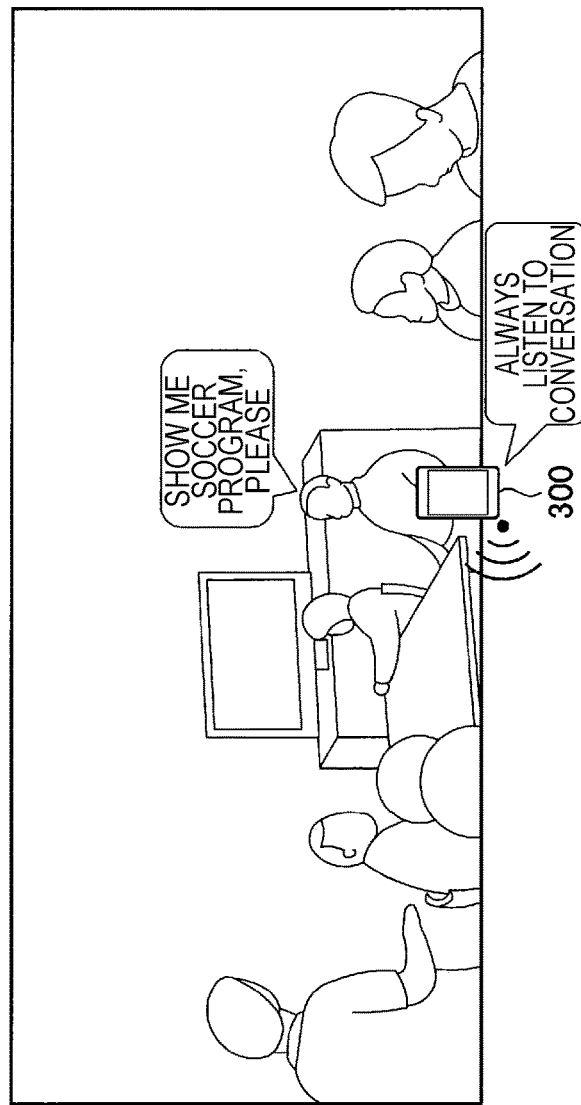
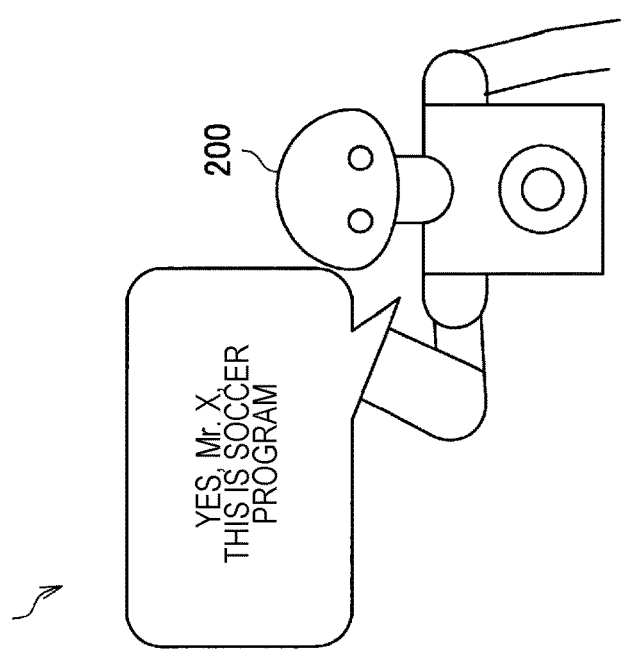

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2015/086549 filed on Dec. 28, 2015, which claims priority benefit of Japanese Patent Application No. JP 2015-073744 filed in the Japan Patent Office on Mar. 31, 2015. Each of the above-referenced applications is hereby incorporated herein by reference in its entirety.

TECHNICAL FIELD

The present disclosure relates to an information processing apparatus, an information processing method, and a program.

BACKGROUND ART

Technologies for communication between an apparatus and another apparatus are under development. As a technology through which one apparatus recognizes a presence of another apparatus according to communication between a wearable apparatus used by being worn on a human body and an apparatus arranged in an environment, a technology disclosed in Patent Literature 1 below may be exemplified.

CITATION LIST

Patent Literature

Patent Literature 1: JP 2005-005787A

DISCLOSURE OF INVENTION

Technical Problem

For example, a user authentication system has been propagated for the purposes of ensuring security, providing services adapted to individual users, and the like. As methods for authenticating a user, for example, there are a method by which a user performs a manipulation for authentication, such as inputting a password, a method of detecting an apparatus corresponding to an authentication key through wireless communication and a biometric method using bio-information.

However, when the method by which a user performs a manipulation such as inputting a password for authentication is used, a burden may be imposed on the user. Further, when the method of detecting an apparatus corresponding to an authentication key through wireless communication is used, authentication may be completed only when an apparatus corresponding to a key is located in a range in which communication can be performed. Furthermore, when the biometric method using bio-information is used, bio-information needs to be registered in advance, and thus a burden may be imposed on a user.

Accordingly, it may not necessarily be possible to improve user convenience even when the aforementioned conventional user authentication methods are used because ensuring security, providing services adapted to individual users, and the like may not necessarily be realized.

The present disclosure proposes a novel and enhanced information processing apparatus, information processing method and program which can improve user convenience.

Solution to Problem

According to the present disclosure, there is provided an information processing apparatus including a processing unit configured to perform a predetermined process on the basis of first information about a user that is acquired by a first apparatus from around a body of the user, and second information about a user that is acquired by a second apparatus different from the first apparatus.

In addition, according to the present disclosure, there is provided an information processing method executed by an information processing apparatus, the information processing method including a step of performing a predetermined process on the basis of first information about a user that is acquired by a first apparatus from around a body of the user, and second information about a user that is acquired by a second apparatus different from the first apparatus.

In addition, according to the present disclosure, there is provided a program for causing a computer to execute a step of performing a predetermined process on the basis of first information about a user that is acquired by a first apparatus from around a body of the user, and second information about a user that is acquired by a second apparatus different from the first apparatus.

Advantageous Effects of Invention

According to the present disclosure, it is possible to improve user convenience.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 2 is a flowchart illustrating a first example of a process related to the information processing method according to the present embodiment.

FIGS. 3A, 3B and 3C are explanatory diagrams of an example of tables used in a process related to the information processing method according to the present embodiment.

FIG. 7 is an explanatory diagram of a first use case to which the information processing method according to the present embodiment is applicable.

FIG. 9 is an explanatory diagram of a second use case to which the information processing method according to the present embodiment is applicable.

FIGS. 15A and 15B are explanatory diagrams of a fifth use case to which the information processing method according to the present embodiment is applicable.

MODE(S) FOR CARRYING OUT THE INVENTION

Figure 1:
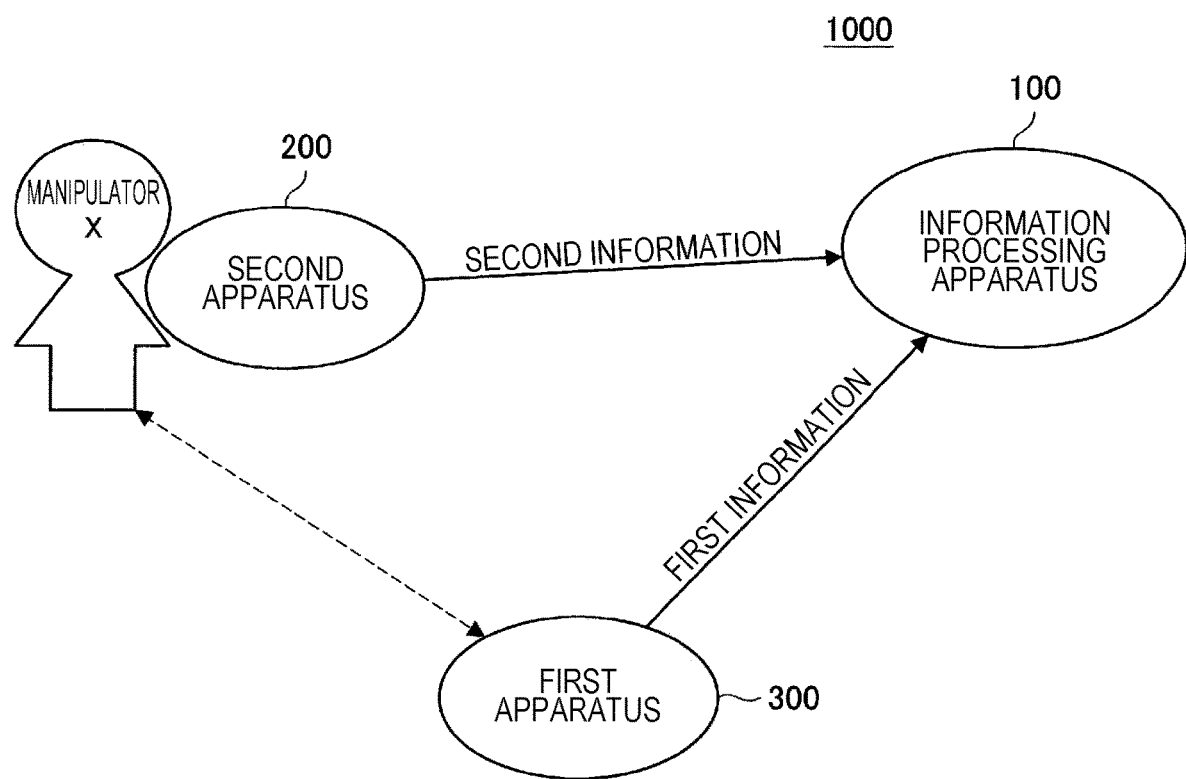
FIG. 1 is an explanatory diagram of an overview of an information processing method according to the present embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Meanwhile, description will be given in the following order.
1. Information processing method according to present embodiment
2. Information processing apparatus according to present embodiment
3. Program according to present embodiment (Information Processing Method According to Present Embodiment)

Prior to description of a configuration of an information processing apparatus according to the present embodiment, an information processing method according to the present embodiment will be described first. Hereinafter, the information processing method according to the present embodiment will be described using an example in which processes related to the information processing method according to the present embodiment are performed by the information processing apparatus according to the present embodiment.

[1] Overview of Information Processing Method According to Present Embodiment

As described above, it may not necessarily be possible to improve user convenience even when a conventional user authentication method is used because ensuring security and providing services adapted to individual users may not necessarily be realized.

Accordingly, for example, the information processing apparatus according to the present embodiment performs a predetermined process on the basis of first information about a user, which is acquired from around the body of the user in a first apparatus, and second information about a user, which is acquired in a second apparatus different from the first apparatus. Hereinafter, information about a user acquired from the first apparatus is referred to as "first information" and information about a user acquired from the second apparatus is referred to as "second information."

More specifically, for example, the information processing apparatus according to the present embodiment compares the first information acquired from the first apparatus or information based on the first information with the second information acquired from the second apparatus or information based on the second information to perform a predetermined process.

FIG. 1 is an explanatory diagram of an overview of the information processing method according to the present embodiment and illustrates an example of an information processing system 1000 according to the present embodiment including an information processing apparatus 100 that performs processes related to the information processing method according to the present embodiment.

For example, the information processing system 1000 includes the information processing apparatus 100, a second apparatus 200 and a first apparatus 300.

Meanwhile, the information processing system according to the present embodiment may include a plurality of first apparatuses and/or a plurality of second apparatuses. A plurality of first apparatuses included in the information processing system according to the present embodiment may be collectively called a "second apparatus 200" or one of second apparatuses included in the information processing system according to the present embodiment may be represented as the "second apparatus 200" in the following description. Further, a plurality of first apparatuses included in the information processing system according to the present embodiment may be collectively called a "first apparatus 300" or one of first apparatuses included in the information processing system according to the present embodiment may be represented as the "first apparatus 300" in the following description.

Hereinafter, the overview of the information processing method according to the present embodiment will be described using the information processing system 100 illustrated in FIG. 1 as an example.

[1-1] Second Apparatus 200

The second apparatus 200 is an apparatus used by a user, for example. For example, the second apparatus 200 has a "function of acquiring the second information" using a sensor included therein, an external sensor connected thereto, or the like and a "function of transmitting the second information" using a communication device included therein or an external sensor connected thereto.

Meanwhile, in the information processing system according to the present embodiment, for example, the information processing apparatus 100 and the second apparatus 200 may be the same apparatus. When the information processing apparatus 100 and the second apparatus 200 are the same apparatus, the second apparatus 200 may not have the "function of transmitting the second information."

As the second apparatus 200, for example, various apparatuses, such as an apparatus corresponding to a target of a user manipulation for locking or unlocking a key of a lockable door and an apparatus used when a user is provided with a service, may be exemplified. Specific examples of the second apparatus 200 will be described in use cases to which the information processing method according to the present embodiment is applied, which will be described below.

[1-2] First Apparatus 300

The first apparatus 300 is an apparatus different from the second apparatus 200. For example, the first apparatus 300 has a "function of acquiring the first information" using a sensor included therein, an external sensor connected thereto, or the like and a "function of transmitting the first information" using a communication device included therein or an external sensor connected thereto.

As the first apparatus 300, for example, apparatuses of types shown in (a) to (c) below, which are able to acquire the first information from surroundings of the body of a user, may be exemplified. When the first apparatus 300 is an apparatus of the type shown in (a) below, for example, the first information is information acquired from the body of the user carrying the first apparatus 300. In addition, when the first apparatus 300 is an apparatus of any of the types shown in (b) and (c) below, for example, the first information is information acquired from the body of the user in contact with the first apparatus 300. Of course, the first apparatus 300 is not limited to the apparatuses of the types shown in (a) to (c) below. Specific examples of the first apparatus 300 will be described in the use cases to which the information processing method according to the present embodiment is applied, which will be described below.

(a) First example of first apparatus 300: apparatuses of types used by being worn on body Wrist-watch-type apparatus Eyeglasses-type apparatus Clothes-type, shoes-type and hat-type apparatuses Apparatuses of accessory types such as ring type, bracelet type and nail types (b) Second example of first apparatus 300: apparatuses of types in contact with human body Sofa-type and chair-type apparatuses Table-type and desk-type apparatuses Vehicle steering wheel-type and parking brake-type apparatuses Keyboard-type and mouse-type apparatuses (c) Third example of first apparatus 300: portable apparatuses Cellular phone-type and smartphone-type apparatuses Key-type apparatuses Bag-type apparatuses

[1-3] Information Processing Apparatus 100

The information processing apparatus 100 performs processes related to the information processing method according to the present embodiment. Meanwhile, for example, as described above, the information processing apparatus 100 and the second apparatus 200 may be the same apparatus in the information processing system according to the present embodiment. A case in which the information processing apparatus 100 and the second apparatus 200 are separate apparatuses as illustrated in FIG. 1 will be exemplified.

As described above, the information processing apparatus 100 compares the second information acquired from the second apparatus 200 or information based on the second information with the first information acquired from the first apparatus 300 or information based on the first information to perform a predetermined process.

The information processing apparatus 100 acquires the second information and the first information, for example, by performing communication with the second apparatus 200 and the first apparatus 300 through a communication unit (which will be described below) included in the information processing apparatus 100 or an external communication device connected to the information processing apparatus 100. For example, communication between the information processing apparatus 100 and the second and first apparatuses 200 and 300 is performed in a wireless or wired manner via a network (or directly). In addition, communication between the information processing apparatus 100 and the second and first apparatuses 200 and 300 may be performed, for example, through another apparatus serving as a relay apparatus.

Here, the second information according to the present embodiment is data indicating a detection result of a sensor included in the second apparatus 200 or an external sensor connected to the second apparatus 200, for example. As a sensor related to the second information, for example, an imaging device (an image sensor), a motion detection sensor such as a pressure sensor or a capacitive sensor, a voice detection sensor such as a microphone, or the like may be exemplified. Further, the sensor related to the second information according to the present embodiment is not limited to the aforementioned examples and may be any sensor capable of acquiring information based on the second information according to the present embodiment, which will be described below.

As the second information according to the present embodiment, for example, one or more of bio-information of a user, information indicating a motion and information related to a behavior history may be exemplified. Specific examples of the second information according to the present embodiment will be described below.

In addition, the information based on the second information according to the present embodiment is data based on the second information. For example, the information based on the second information according to the present embodiment may be the second information itself or information indicating a value or a waveform specified by the second information, a value or a waveform estimated therefrom, or the like.

As the information based on the second information according to the present embodiment, for example, one or more of bio-information of a user, information indicating a motion and information related to a behavior history, which are specified (or estimated) on the basis of the second information, may be exemplified. Specific examples of the information based on the second information according to the present embodiment will be described below.

In addition, the first information according to the present embodiment is data indicating a detection result of a sensor included in the first apparatus 300 or an external sensor connected to the first apparatus 300, for example. As a sensor related to the first information, for example, a position detection device or the like, such as a pulse wave sensor, a myoelectric sensor, an imaging device (image sensor), a Global Positioning System (GPS) device or the like, may be exemplified. Further, the sensor related to the first information according to the present embodiment is not limited to the aforementioned examples and may be any sensor capable of acquiring information based on the first information according to the present embodiment, which will be described below.

As the first information according to the present embodiment, for example, one or more of bio-information of a user, information indicating a motion and information related to a behavior history may be exemplified. Specific examples of the first information according to the present embodiment will be described below.

Furthermore, the information based on the first information according to the present embodiment is data based on the first information. For example, the information based on the first information according to the present embodiment may be the first information itself or information indicating a value or a waveform specified by the first information, a value or a waveform estimated therefrom, or the like.

As the information based on the first information according to the present embodiment, for example, one or more of bio-information of a user, information indicating a motion and information related to a behavior history, which are specified (or estimated) on the basis of the first information, may be exemplified. Specific examples of the information based on the first information according to the present embodiment will be described below.

The information processing apparatus 100 compares the first information or information based on the first information with the second information corresponding to the first information or information based on the second information. Hereinafter, a case in which information corresponding to comparison targets by the information processing apparatus 100 is information based on the first information and information based on the second information will be described as an example. Meanwhile, the information based on the first information may be the first information itself and the information based on the second information may be the second information itself, for example, as described above. As an example of information (information based on the second information and corresponding information based on the first information) corresponding to comparison targets by the information processing apparatus 100 and an example of a combination of the second information and the first information from which the information can be acquired, examples shown in (A) to (C) below may be exemplified, for example.

(A) First Example of Information Corresponding to Comparison Targets: Static Information (Bio-Information)

(A-1) Value indicating pulse wave characteristic (e.g., heart rate) and waveform of pulse wave characteristic specified by value indicating pulse wave characteristic Second information: captured image data obtained by capturing an image of a part (e.g., a skin part such as a hand) used for manipulation of the second apparatus 200, and the like First information: data indicating a detection result of a pulse wave sensor, and the like (A-2) Information representing shape of part used for manipulation Second information: captured image data obtained by capturing an image of a part (e.g., a hand or the like) used for manipulation of the second apparatus 200, and the like First information: data indicating a detection result of a myoelectric sensor, and the like (A-3) Value indicating respiration (e.g., value indicating respiration rate (breathing rate) in predetermined period) and respiration waveform specified by value indicating respiration Second information: captured image data obtained by capturing an image of the chest connected to a part (e.g., a hand or the like) used for manipulation of the second apparatus 200, and the like First information: data indicating a detection result of a chest sensor, data indicating a detection result of a sound detection sensor for detecting a sound of respiration, and the like (A-4) Value indicating body temperature and waveform of body temperature waveform specified by value indicating body temperature Second information: data indicating a detection result of a thermograph for measuring the temperature of a part (e.g., a hand or the like) used for manipulation of the second apparatus 200, and the like First information: data indicating a detection result of a body temperature sensor, and the like (A-5) Information indicating characteristics of clothes and skin Second information: captured image data obtained by capturing an image of clothes or skin connected to a part (e.g., a hand or the like) used for manipulation of the second apparatus 200, and the like First information: captured image data obtained by capturing an image of clothes or skin of a person carrying the first apparatus 300, and the like (A-6) Combination of two or more of (A-1) to (A-5)

(B) Second Example of Information Corresponding to Comparison Targets: Dynamic Information (Information Indicating Motion)

(B-1) Trace of motion of manipulation (e.g., trace of motion such as flicking, tapping, or gesture such as virtual object manipulation)

Second information: data indicating content of a performed manipulation, data that can be used to estimate content of a manipulation, and the like First information: data indicating a detection result of a sensor such as a speed sensor or a myoelectric sensor, and the like (C) Third Example of Information Corresponding to Comparison Targets: Pre-Context (Information Related to Behavior History)

(C-1) Information indicating preference

Second information: data indicating content of a performed manipulation, and the like First information: data indicating a purchase history, and the like (C-2) Information indicating content of previous conversation Second information: data indicating a detection result of a voice detection sensor, data indicating content of a manipulation performed according to voice, and the like First information: data indicating a detection result of a voice detection sensor, and the like (C-3) Information indicating previously performed motion Second information: data indicating content of a performed manipulation, and the like First information: data indicating a detection result of a position detection device, and the like, and data capable of estimating a behavior of a person carrying the first apparatus 300, and the like (e.g., traveling, jogging, leaving work and the like of the person carrying the first apparatus are estimated by using data indicating detection results of the position detection device)

(C-4) Combination of two or more of (C-1) to (C-3)

As an example of information corresponding to comparison targets by the information processing apparatus 100 and an example of a combination of the second information and the first information from which the information can be acquired, for example, the aforementioned examples shown in (A) to (C) may be exemplified.

As shown in the aforementioned examples of (A) to (C), the second information and the first information may be information indicating the same types of content or information indicating different content, for example. As a combination of the second information and the first information, a combination of any information from which information based on the first information and information based on the second information, which can be compared with each other, can be acquired may be exemplified.

Meanwhile, an example of information corresponding to comparison targets by the information processing apparatus 100 and an example of a combination of the second information and the first information from which the information can be acquired are not limited to the aforementioned examples shown in (A) to (C). For example, an example of information corresponding to comparison targets by the information processing apparatus 100 may be post-context (another example of information about a behavior history) in a period from a start time of a certain detection until a predetermined period elapses.

As a predetermined process performed for the information processing apparatus 100 to compare information based on the first information with information based on the second information, for example, a user authentication process may be exemplified.

For example, the information processing apparatus 100 determines whether a user corresponding to the second information is identical to a user corresponding to the first information by comparing information based on the first information with information based on the second information. Here, the determination depending on comparison of the information based on the first information (or the first information) with the information based on the second information (or the second information) corresponds to a process of authenticating whether the user corresponding to the second information is identical to the user corresponding to the first information. For example, a case in which it is determined that the user corresponding to the second information acquired from the second apparatus 200 is identical to the user corresponding to the first information acquired from the first apparatus 300 corresponds to a case in which authentication has been performed normally (a case in which authentication has been completed).

Here, for example, the determination of whether the users are identical corresponds to a determination of whether a user who uses the second apparatus 200 is identical to a user who carries the first apparatus 300.

Accordingly, for example, the information processing apparatus 100 can achieve effects as described in (I) to (IV) below by comparing the information based on the first information with the information based on the second information to perform an authentication process as a predetermined process.

(I) First Example of Effects Achieved by Performing Authentication Process as Predetermined Process By comparing information based on the first information with information based on the second information to perform an authentication process through the information processing apparatus 100, for example, a user can complete authentication simply by carrying the first apparatus 300, such as by wearing the first apparatus 300 on his/her body.

Accordingly, it is possible to realize a system (e.g., a system with respect to a door that can be opened by a user merely wearing a wrist watch, or the like) which does not require a manipulation for authentication, such as a password input manipulation or a manipulation using a physical key, by comparing the information based on the first information with the information based on the second information to perform an authentication process through the information processing apparatus 100.

(II) Second Example of Effects Achieved by Performing Authentication Process as Predetermined Process For example, the information processing apparatus 100 can determine whether a person who manipulates the second apparatus 200 is identical to a person who carries the first apparatus 300 by comparing information based on the first information with information based on the second information to perform an authentication process.

Accordingly, it is possible to prevent authentication from being completed only when an apparatus corresponding to a key is located within a range in which communication can be performed as in a case in which the aforementioned method of detecting an apparatus corresponding to an authentication key through wireless communication is used. That is, even if there are a plurality of persons near the second apparatus 200, the information processing apparatus 100 can authenticate a user who manipulates the second apparatus 200 while carrying the first apparatus 300.

(III) Third Example of Effects Achieved by Performing Authentication Process as Predetermined Process Since the information processing apparatus 100 compares information based on the first information with information based on the second information to perform an authentication process, a user need not register his or her bio-information in advance even when the information based on the first information and the information based on the second information are bio-information.

Accordingly, the information processing apparatus 100 compares the information based on the first information with the information based on the second information to perform an authentication process, to thereby prevent a burden from being imposed on the user as in a case in which the aforementioned biometric method using bio-information is employed.

(IV) Fourth Example of Effects Achieved by Performing Authentication Process as Predetermined Process The information processing apparatus compares information based on the second information, which is based on the second information, with information based on the first information, which is based on the first information, to perform an authentication process. Here, the information processing apparatus 100 acquires the second information and the first information by performing communication with the second apparatus 200 and the first apparatus 300, respectively, through a communication unit (which will be described below) and the like. In addition, communication related to acquisition of the second information and the first information is not limited to specific communication such as communication through the human body.

Accordingly, it is possible to apply the information processing method according to the present embodiment to various systems, such as a system using a user interface (UI) without a contact of a keyboard, a mouse and the like on the human body by comparing information based on the second information, which is based on information about one user, with information based on the first information, which is based on the first information, to perform an authentication process through the information processing apparatus 100.

Meanwhile, the authentication process performed by the information processing apparatus 100 as a predetermined process is not limited to the "process of authenticating whether a user corresponding to the second information is identical to a user corresponding to the first information" (process of determining whether a user who uses the second apparatus 200 is identical to a user who carries the first apparatus 300).

For example, when information indicating the first apparatus is further acquired from the first apparatus 300, the information processing apparatus 100 acquires third information corresponding to a user who carries the first apparatus 300 on the basis of the acquired information indicating the first apparatus. In addition, the information processing apparatus 100 further compares the acquired third information with the second information or information based on the second information. Then, the information processing apparatus 100 may further determine whether a user corresponding to the second information is identical to a user who carries the first apparatus 300 corresponding to the third information, as a predetermined process.

Here, as the information indicating the first apparatus according to the present embodiment, for example, any data capable of specifying the first apparatus 300, such as the ID of the first apparatus 300 or a media access control (MAC) address of a communication device included in the first apparatus 300, may be exemplified.

Furthermore, as the third information according to the present embodiment, for example, information based on the first information, which is specified on the basis of the information indicating the first apparatus, may be exemplified.

The information processing apparatus 100 acquires the first information or information based on the first information, which is associated with the acquired information indicating the first apparatus, with reference to "data in which the first information or the information based on the first information and the information indicating the first apparatus are associated and recorded," for example.

Here, for example, data in any form in which the first information or the information based on the first information can be associated with the information indicating the first apparatus, such as a table or a database in which the first information or the information based on the first information is associated with the information indicating the first apparatus may be exemplified as "data in which the first information or the information based on the first information and the information indicating the first apparatus are associated and recorded." Hereinafter, a case in which "data in which the first information or the information based on the first information and the information indicating the first apparatus are associated and recorded" is data in a table form will be described as an example.

The "data in which the first information or the information based on the first information and the information indicating the first apparatus are associated and recorded" is stored in a recording medium such as a storage unit (which will be described below) included in the information processing apparatus 100 or an external recording medium connected to the information processing apparatus 100, for example.

Furthermore, the information processing apparatus 100 updates the "data in which the first information or the information based on the first information and the information indicating the first apparatus stored in a recording medium are associated and recorded," for example, whenever the information indicating the first apparatus and the first information are acquired from the first apparatus 300. Here, update of the data includes new generation of data and overwriting update of data (e.g., addition, deletion, change and the like of a record of a table), for example. Further, a process related to update of the data may be performed in an external apparatus of the information processing apparatus 100, for example, a server.

For example, the "data in which the first information or the information based on the first information and the information indicating the first apparatus stored in a recording medium are associated and recorded" is updated as described above, and thus a likelihood of the first information or the information based on the first information, which is associated with the information indicating the first apparatus, in the data being information (data) corresponding to a user who frequently uses the first apparatus 300, that is, a user who carries the first apparatus 300, increases.

An example of the authentication process based on the acquired information indicating the first apparatus will be described in more detail.

For example, when the first information is acquired from the table or the like on the basis of the information indicating the first apparatus, the information processing apparatus 100 regards information specified (or information estimated) on the basis of the first information acquired from the table or the like as the third information. As a specific example, for example, when data (an example of the first information) indicating a detection result of a pulse wave sensor is acquired from the table or the like, the information processing apparatus 100 specifies a value or a waveform indicating a pulse wave characteristic from the data indicating the detection result of the pulse wave sensor and regards data indicating the specified value or waveform indicating the pulse wave characteristic as the third information.

In addition, for example, when the information based on the first information is acquired from the table or the like on the basis of the information indicating the first apparatus, the information processing apparatus 100 regards the information based on the first information acquired from the table or the like as the third information. As a specific example, for example, when data (an example of the information based on the first information) indicating a value or a waveform indicating a pulse wave characteristic is acquired from the table or the like, the information processing apparatus 100 regards the data indicating the value or waveform indicating the pulse wave characteristic as the third information.

The information processing apparatus 100 acquires the third information on the basis of the information indicating the first apparatus as described above, for example. Here, a likelihood of the acquired third information being information corresponding to the user who carries the first apparatus 300 is high, as described above. Accordingly, the information processing apparatus 100 can further determine whether the user corresponding to the second information is identical to the user who carries the first apparatus 300 corresponding to the third information by comparing the second information or information based on the second information with the acquired third information.

When an authentication process using the third information is performed, the information processing apparatus 100 determines that authentication has been performed normally, that is, authentication has been completed, for example, when "the user corresponding to the second information acquired from the second apparatus 200 is identical to the user corresponding to the first information acquired from the first apparatus 300, and the user corresponding to the second information is identical to a user who carries the first apparatus 300 corresponding to the acquired third information."

Even when the authentication process using the third information is performed, authentication according to comparison of information based on the first information (or the first information) with information based on the second information (or the second information) is performed, and thus the effects described above in (I) to (IV) can be achieved. Furthermore, when the authentication process using the third information is performed, whether the user corresponding to the second information is identical to the user who carries the first apparatus 300 corresponding to the third information is authenticated, and thus more thorough authentication can be performed.

For example, the information processing apparatus 100 performs the aforementioned authentication process as a predetermined process.

The aforementioned authentication process is performed as the predetermined process so that the above-described effects described in (I) to (IV) are achieved. Accordingly, the information processing apparatus 100 can improve user convenience by performing the aforementioned authentication process as the predetermined process.

Meanwhile, the predetermined process according to the present embodiment is not limited to the aforementioned authentication process.

For example, the information processing apparatus 100 may switch the predetermined process on the basis of a user authentication result, such as "whether a user corresponding to the first information is identical to a user corresponding to the second information" or "whether a user corresponding to the second information acquired from the second apparatus 200 is identical to a user corresponding to the first information acquired from the first apparatus 300, and the user corresponding to the second information is identical to a user who carries the first apparatus 300 corresponding to the acquired third information," through the authentication process using the third information.

For example, when it is determined that the users are not identical as a user authentication result, the information processing apparatus 100 does not perform the process that is performed when it is determined that the users are identical.

Furthermore, when it is determined that the users are not identical, the information processing apparatus 100 may perform a process of controlling an error notification (i.e., authentication error notification) indicating that it is determined that the users are not identical. For example, the information processing apparatus 100 causes the corresponding apparatus (information processing apparatus 100) or an external apparatus to perform the notification. As an example of the error notification, for example, a visual notification displaying characters or images on a display screen, an auditory notification outputting a sound through a sound output device such as a speaker, or a combination of such notifications may be exemplified.

In addition, for example, when it is determined that the users are identical through a user authentication result, that is, when authentication has been completed in the authentication process, the information processing apparatus 100 may further cause a process corresponding to the user authenticated through the authentication process to be performed.

As a control target to be caused to perform the process targeted for the authenticated user by the information processing apparatus 100, for example, one or both of the corresponding apparatus (information processing apparatus 100) and an external apparatus of the information processing apparatus 100 may be exemplified. When the information processing apparatus 100 is the corresponding apparatus, the information processing apparatus 100 performs the process corresponding to the user authenticated through the authentication process. Further, when the information processing apparatus 100 is an external apparatus, the information processing apparatus 100 causes a communication unit (which will be described below) or the like to transmit a signal including a command for performing the process corresponding to the authenticated user to the external apparatus such that the external apparatus performs the process corresponding to the authenticated user.

As the process corresponding to the authenticated user, for example, any process performed for the authenticated user, such as a previously set fixed process such as unlocking or a process associated with the authenticated user, may be exemplified.

When the process corresponding to the authenticated user is a previously set fixed process, the fixed process is specified as a process performed for the authenticated user.

In addition, when the process corresponding to the authenticated user is a process associated with the authenticated user, the information processing apparatus 100 specifies the process performed for the authenticated user, for example, using a table (or a database) in which information indicating users, such as user IDs, is associated with information about executable processes. For example, when information about executable processes is data indirectly indicating processes to be performed and data directly indicating processes to be performed, such as data indicating services provided to users, the information processing apparatus 100 specifies a process corresponding to a service provided to the user or a process indicated by data directly indicating a process to be performed as the process targeted for the authenticated user. Furthermore, when the information about the executable processes is data indicating authority, the information processing apparatus 100 specifies a process in a range of user's authority indicated by data indicating authority as the process targeted for the authenticated user.

Then, the information processing apparatus 100 causes a control target to perform the specified process for the authenticated user.

A process related to control of execution of the above-described process corresponding to the authenticated user is performed as a predetermined process, so that a service or the like corresponding to the user authenticated through the authentication process can be provided to the user.

Accordingly, the information processing apparatus 100 can improve user convenience even when a process related to execution control is further performed as a predetermined process.

In a specific example, as a predetermined process performed when it is determined that the user corresponding to the first information is identical to the user corresponding to the second information, for example, a process that enables a manipulation specific to a user may be exemplified.

Here, as the process that enables a manipulation specific to a user, processes described in (i) to (iii) below may be exemplified. Of course, examples of the process that enables a manipulation specific to a user are not limited to the processes described in (i) to (iii) below.

(i) First Example of Process that Enables Manipulation Specific to User

As a process that enables a manipulation specific to a user according to the first example, for example, a process of switching to a state in which a manipulation corresponding to a user can be performed may be exemplified. In a specific example, as the process of switching to a state in which a manipulation corresponding to a user can be performed, for example, a process of logging an authenticated user in to a system, a process of switching to a state in which an apparatus can be used, a process of causing a specific application to be available, or the like may be exemplified. The process that enables a manipulation specific to a user according to the first example is performed so that the user can use the apparatus or the system in a usage environment corresponding to him or her. Furthermore, the process that enables a manipulation specific to a user according to the first example may be applied, for example, to a third use case which will be described below, and the like.

(ii) Second Example of Process that Enables Manipulation Specific to User

As a process that enables a manipulation specific to a user according to the second example, for example, a process that enables manipulation of a target associated with a user may be exemplified. In a specific example, as the process that enables manipulation of a target associated with a user, for example, a process of allocating a target related to a manipulation to a user, such as a process of enabling manipulation of a target related to a UI, such as a cursor, may be exemplified. The process that enables a manipulation specific to a user according to the second example is performed so that manipulation of a UI by each user through a cursor for each user is realized, for example, in a case in which the UI is manipulated by a plurality of users. Furthermore, the process that enables a manipulation specific to a user according to the second example may be applied, for example, to a fourth use case which will be described below.

(iii) Third Example of Process that Enables Manipulation Specific to User

As a process that enables a manipulation specific to a user according to the second example, for example, a process of performing a manipulation of locking or unlocking a target associated with a user may be exemplified. As a target associated with a user, for example, any physical target that the user has authority to lock or unlock, such as a safe described in use cases which will be described below, may be exemplified. Furthermore, the process of performing a manipulation of locking or unlocking a target associated with a user may include, for example, a process of causing an external apparatus to perform a process related to locking of the target or a process related to unlocking of the target. The process that enables a manipulation specific to a user according to the third example may be applied, for example, to a first use case, a second use case, and the like, which will be described below.

The information processing apparatus 100 performs, for example, the above-described processes as processes related to the information processing method according to the present embodiment. Here, the above-described processes related to the information processing method according to the present embodiment are performed so that the aforementioned effects described in (I) to (IV) are achieved.

Accordingly, the information processing apparatus 100 can improve user convenience.

[2] Specific Examples of Processes Related to Information Processing Method According to Present Embodiment Next, specific examples of the above-described processes related to the information processing method according to the present embodiment will be described. A case in which the information processing apparatus 100 constituting the information processing system 1000 shown in FIG. 1 performs processes related to the information processing method according to the present embodiment will be described below as an example.

[2-1] First Example of Processes Related to Information Processing Apparatus According to Present Embodiment FIG. 2 is a flowchart illustrating the first example of processes related to the information processing method according to the present embodiment. Here, FIG. 2 illustrates an example in which the information processing apparatus 100 performs the authentication process and the process related to execution control as predetermined processes.

The information processing apparatus 100 determines whether the second information and the first information are acquired (S100).

Until a predetermined set time elapses after one of the first information and the second information is acquired, for example, the information processing apparatus 100 determines that the first information and the second information have been acquired when the other information has been acquired. Here, the predetermined time may be a previously set fixed time (period) or a variable time that can be appropriately set by a manipulation or the like of the user of the information processing apparatus 100, or the like.

When it is determined that the first information and the second information have not been acquired in step S100, the information processing apparatus 100 does not perform processes in step S102 until it is determined that the first information and the second information have been acquired.

On the other hand, when it is determined that the first information and the second information are acquired in step S100, the information processing apparatus 100 compares information based on the first information with information based on the second information, which corresponds to the information based on the first information (or the first information) (S102).

For example, when the information based on the first information and the information based on the second information are values indicating pulse wave characteristics described in (A-1) above, the information processing apparatus 100 compares a pulse wave value (an example of the information based on the second information) specified from a captured image, which corresponds to the second information, with a pulse wave value (an example of the information based on the first information) indicated by a detection result of a pulse wave sensor, which corresponds to the first information.

In addition, for example, when the information based on the first information and the information based on the second information are information indicating a shape of a part used for manipulation, described in (A-2) above, the information processing apparatus 100 compares a myoelectric value specified from a captured image, which corresponds to the second information, with a myoelectric value indicated by a detection result of a myoelectric sensor, which corresponds to the first information.

Even when the information based on the first information and the information based on the second information are information described in (A-3) to (C-3) above, the information processing apparatus 100 compares the information based on the first information and the information based on the second information, which correspond to each other, as in the cases described in (A-1) and (A-2) above.

The information processing apparatus 100 determines whether a user corresponding to the first information is identical to a user corresponding to the second information as a result of the process of step S102 (S104). For example, the process of step S104 corresponds to a process of determining whether a user who uses the second apparatus 200 is identical to a user who carries the first apparatus 300.

When it is determined that the user corresponding to the first information is not identical to the user corresponding to the second information in step S104, the information processing apparatus 100 assumes that authentication has not been completed and finishes the processes of FIG. 2. Further, when it is determined that the user corresponding to the first information is not identical to the user corresponding to the second information, the information processing apparatus 100 may perform, for example, a process related to error notification.

On the other hand, when it is determined that the user corresponding to the first information is identical to the user corresponding to the second information in step S104, the information processing apparatus 100 causes a control target to perform a process corresponding to the user determined to be identical, that is, the authenticated user (S106). Here, the information processing apparatus 100 may specify authority of the user, for example, using table 3 shown in FIG. 3C and cause the control target to perform a process corresponding to the authority.

The information processing apparatus 100 performs, for example, the processes shown in FIG. 2 as processes related to the information processing method according to the present embodiment.

When the processes shown in FIG. 2 are performed, the information based on the second information is compared with the corresponding information based on the first information and at least the authentication process is performed as a predetermined process in the information processing apparatus 100. Accordingly, for example, the processes shown in FIG. 2 are performed so that the information processing apparatus 100 can improve user convenience.

Meanwhile, processes related to the information processing method according to the present embodiment are not limited to the processes according to the first example illustrated in FIG. 2.

For example, the information processing apparatus 100 may perform a process using a table stored in a recording medium such as a storage unit (which will be described below).

FIGS. 3A, 3B and 3C are explanatory diagrams of an example of tables used in processes related to the information processing method according to the present embodiment.

FIG. 3A shows an example of a table in which account IDs (an example of information indicating users) and IDs of devices owned by users (an example of information indicating owned devices) are associated. Records of the table shown in FIG. 3A are updated, for example, according to a manipulation of registering a user such as the user of the information processing apparatus 100 or the user of the first apparatus 300, or the like. The table in which account IDs and IDs of devices owned by users are associated, as shown in FIG. 3A, may be represented as "table 1" in the following description.

In addition, FIG. 3B shows an example of a table in which device IDs (an example of information indicating the first apparatus), information on owners, and time when such information is recorded are associated. A record is added to the table shown in FIG. 3B, for example, whenever the first information is acquired from the first apparatus 300. The table in which device IDs (an example of information indicating the first apparatus), information on owners, and times at which such information is recorded are associated, as shown in FIG. 3B, may be represented as "table 2" in the following description.

Further, FIG. 3C shows an example of a table in which account IDs (an example of information indicating users) and information indicating authority are associated. Records of the table shown in FIG. 3C are updated, for example, according to a manipulation of registering a user such as the user of the information processing apparatus 100 or the user of the first apparatus 300. The table in which account IDs and information indicating authority are associated, as shown in FIG. 3C, may be represented as "table 3" in the following description.

Meanwhile, examples of tables used in processes related to the information processing method according to the present embodiment are not limited to the examples shown in FIGS. 3A, 3B and 3C, of course. Processes using the tables shown in FIGS. 3A, 3B and 3C will be described below as examples of processes related to the information processing method according to the present embodiment.

Figure 4:
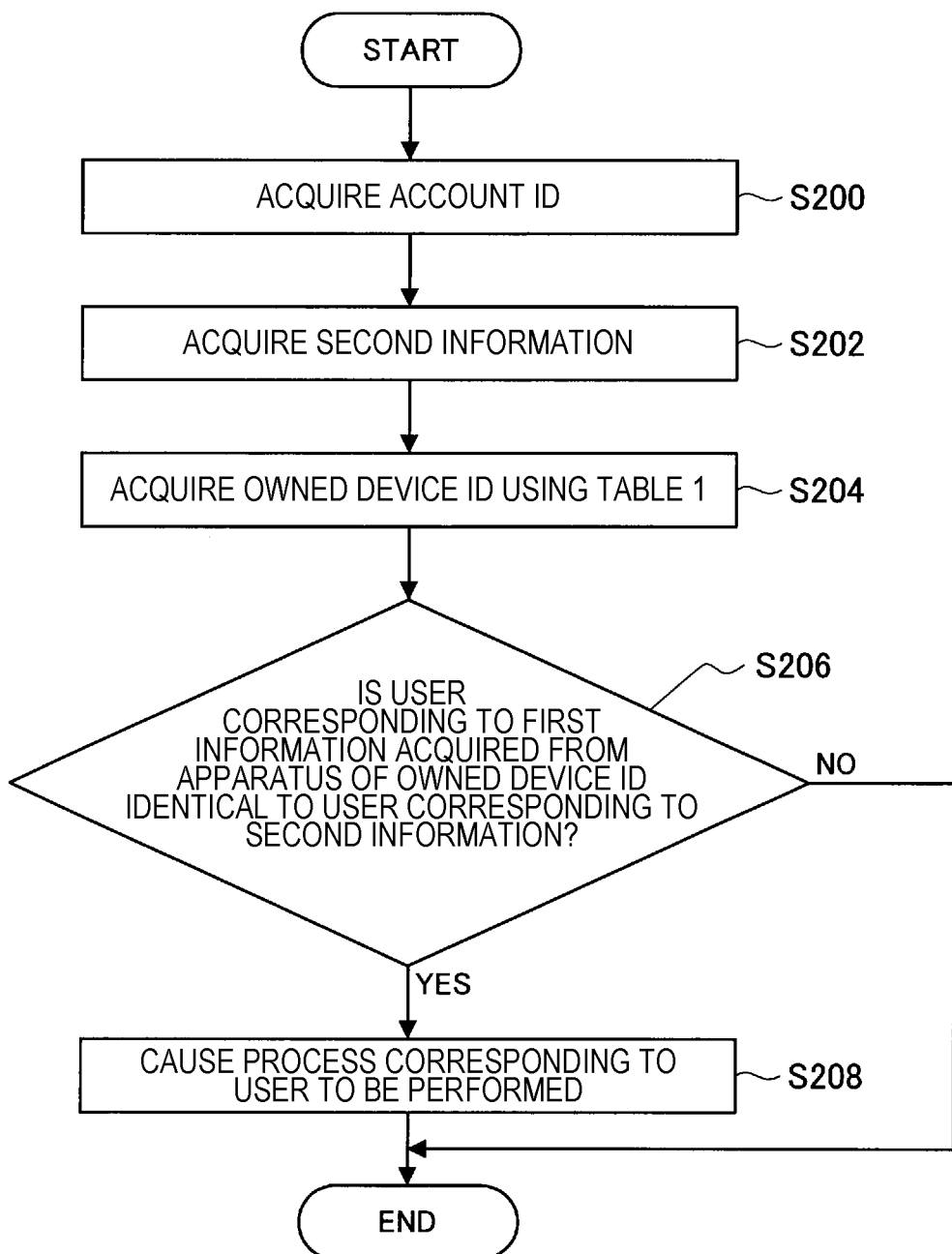
FIG. 4 is a flowchart illustrating a second example of a process related to the information processing method according to the present embodiment.

[2-2] Second Example of Processes Related to Information Processing Method According to Present Embodiment FIG. 4 is a flowchart illustrating the second example of processes related to the information processing method according to the present embodiment and shows an example of processes using tables shown in FIGS. 3A, 3B and 3C. Here, FIG. 4 illustrates an example in which the information processing apparatus 100 performs the authentication process and the process related to execution control as predetermined processes.

The information processing apparatus 100 acquires an account ID from the second apparatus 200 (S200) and acquires the second information (S202). In the second apparatus 200, the account ID is specified, for example, by a user using a fingerprint sensor, inputting a password, or the like.

The information processing apparatus 100 acquires an owned device ID corresponding to the account ID acquired in step S200 with reference to table 1 shown in FIG. 3A (S204).

For example, the information processing apparatus 100 determines whether a user corresponding to the first information acquired from an apparatus (an example of the first apparatus 300) corresponding to the owned device ID is identical to a user corresponding to the second information (S206). In step S206, the information processing apparatus 100 performs processes similar to steps S102 and S104 of FIG. 2 on the basis of information based on the first information, which is based on the first information acquired from the apparatus (an example of the first apparatus 300) corresponding to the owned device ID, and information based on the second information, which is based on the second information.

When it is determined that the user corresponding to the first information is not identical to the user corresponding to the second information in step S206, the information processing apparatus 100 assumes that authentication has not been completed and finishes the processes of FIG. 4. Further, when it is determined that the user corresponding to the first information is not identical to the user corresponding to the second information, the information processing apparatus 100 may perform, for example, a process related to error notification.

On the other hand, when it is determined that the user corresponding to the first information has been identical to the user corresponding to the second information in step S206, the information processing apparatus 100 causes a control target to perform a process corresponding to the user determined to be identical, that is, the authenticated user, for example, as in step S106 of FIG. 2 (S208).

The information processing apparatus 100 performs, for example, the processes illustrated in FIG. 4 as processes related to the information processing method according to the present embodiment.

Even when the processes illustrated in FIG. 4 are performed, the information based on the first information is compared with the corresponding information based on the second information and at least the authentication process is performed as a predetermined process in the information processing apparatus 200, as in the case in which the processes related to the first example illustrated in FIG. 2 are performed. Accordingly, for example, the processes illustrated in FIG. 4 are performed so that the information processing apparatus 100 can improve user convenience.

Meanwhile, the process related to acquisition of a device ID and an account ID using tables is not limited to the example shown in FIG. 4.

Figure 5:
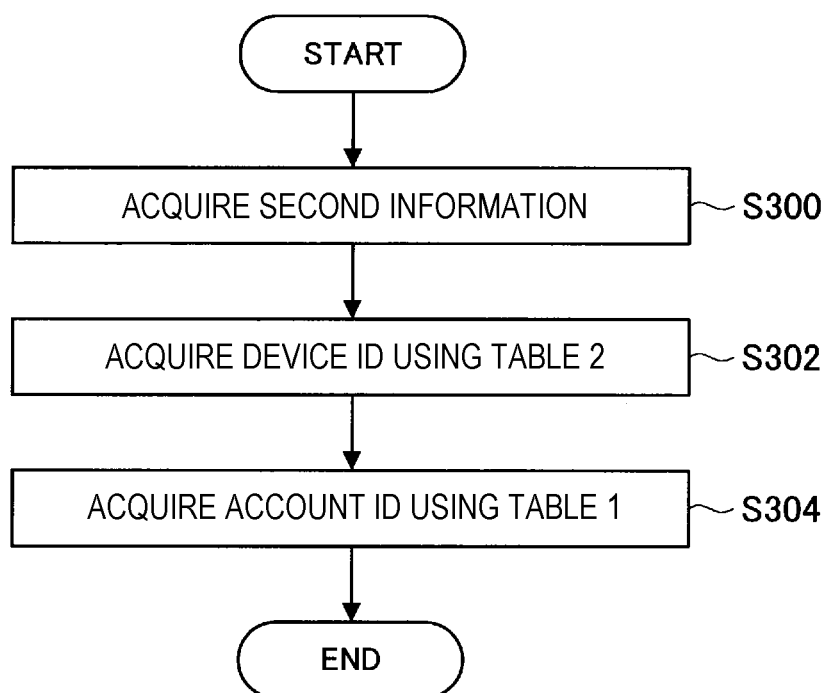
FIG. 5 is a flowchart illustrating an example of a process related to acquisition of a device ID and an account ID using the tables shown in FIGS. 3A, 3B and 3C.

FIG. 5 is a flowchart illustrating an example of the process related to acquisition of a device ID and an account ID using tables shown in FIGS. 3A, 3B and 3C.

The information processing apparatus 100 acquires the second information from the second apparatus (S300).

The information processing apparatus 100 acquires a device ID corresponding to the second information acquired in step S300 with reference to table 2 shown in FIG. 3B (S302). The information processing apparatus 100 acquires the device ID corresponding to the second information by searching table 2 for information on an owner corresponding to the second information and extracting a device ID associated with the owner information found in table 2.

In addition, the information processing apparatus 100 acquires an account ID corresponding to the device ID acquired in step S302 with reference to table 1 shown in FIG. 3A (S304). The information processing apparatus 100 acquires the account ID corresponding to the device ID acquired in step S302 by searching table 1 for a device ID corresponding to the device ID acquired in step S302 and extracting an account ID associated with the device ID found in table 1.

The information processing apparatus 100 can acquire a device ID and an account ID using tables shown in FIGS. 3A, 3B and 3C, for example, by performing the process illustrated in FIG. 5. In addition, the information processing apparatus 100 performs the processes of steps S204 to S208 of FIG. 4 using the acquired device ID and account ID, for example.

Figure 6:
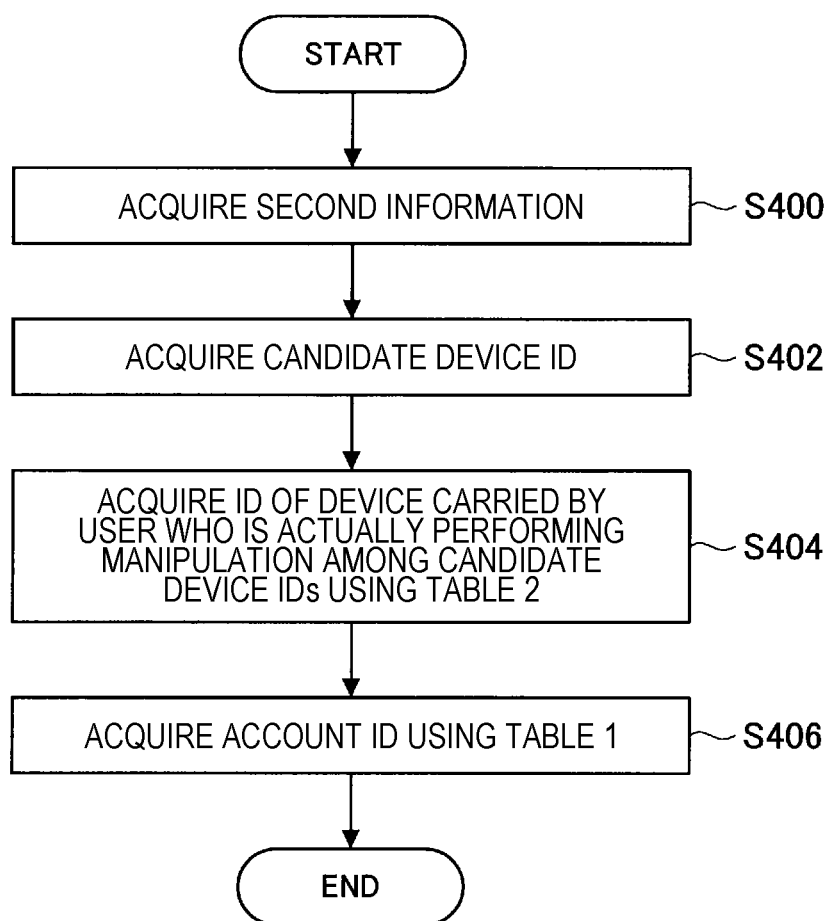
FIG. 6 is a flowchart illustrating another example of the process related to acquisition of a device ID and an account ID using the tables shown in FIGS. 3A, 3B and 3C.

FIG. 6 is a flowchart illustrating another example of the process related to acquisition of a device ID and an account ID using the tables shown in FIGS. 3A, 3B and 3C.

The information processing apparatus 100 acquires the second information from the second apparatus (S400).

The information processing apparatus 100 acquires a candidate device ID from the second apparatus 200 (S402). Here, the second apparatus 200 transmits, for example, a signal including a command for causing a device ID to be transmitted through wireless communication and transmits a device ID, which is transmitted from an apparatus located within the coverage of the wireless communication in response to the command, to the information processing apparatus 100. The device ID transmitted from the second apparatus 200 corresponds to the candidate device ID.

The information processing apparatus 100 acquires a device ID corresponding to the candidate device ID acquired in step S402 with reference to table 2 shown in FIG. 3B (S404). Here, for example, the process of step S404 corresponds to a process of acquiring an ID of a device that is likely to be carried by a person who is actually manipulating the second apparatus 200.

The information processing apparatus 100 acquires an account ID corresponding to the device ID acquired in step S404 with reference to table 1 shown in FIG. 3A as in step S304 of FIG. 5 (S406).

The information processing apparatus 100 can acquire a device ID and an account ID using the tables shown in FIGS. 3A, 3B and 3C, for example, by performing the processes illustrated in FIG. 6. In addition, for example, the information processing apparatus 100 performs the processes of step S204 to S208 of FIG. 4 using the acquired device ID and account ID.

[3] Use Cases to which Information Processing Method According to Present Embodiment is Applied Next, use cases to which the information processing method according to the present embodiment is applicable will be described.

[3-1] First Use Case: Enhanced PIN Safe

Figure 8:
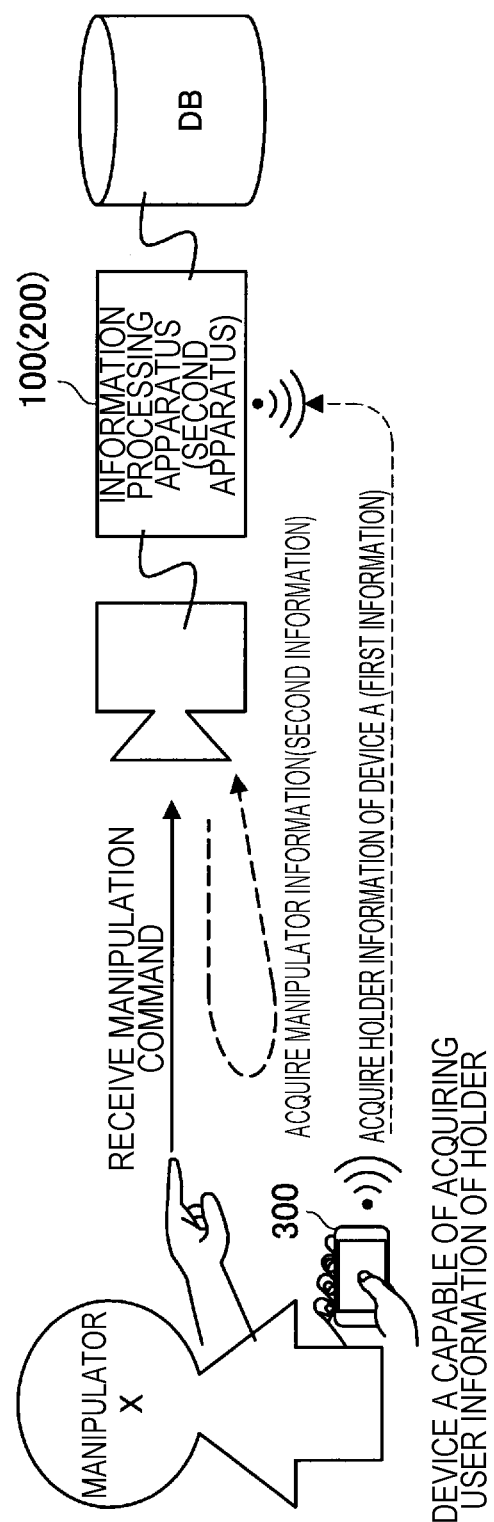
FIG. 8 is an explanatory diagram of the first use case to which the information processing method according to the present embodiment is applicable.

FIGS. 7 and 8 are explanatory diagrams of the first use case to which the information processing method according to the present embodiment is applicable and illustrate a use case applied to an enhanced PIN safe. In the first use case, security is improved through user authentication according to a process related to the information processing method according to the present embodiment in addition to conventional security measures of inputting a PIN.

In the first use case, for example, an apparatus for managing unlocking of a door of a safe corresponds to the information processing apparatus 10 and the second apparatus 200. In addition, for example, an apparatus such as a wrist watch or a smartphone corresponds to the first apparatus 300 in the first use case. Meanwhile, the information processing apparatus 100 and the second apparatus 200 may be separate apparatuses, of course, in the first use case.

An example of a process related to the information processing method according to the present embodiment in the first use case will be described with reference to FIG. 8. The case in which information based on the first information and information based on the second information are values indicating pulse wave characteristics described in (A-1) above will be described below as an example.

When an image of a hand of a manipulator X who inputs a PIN is captured by an image sensor configured of an imaging device or the like, the information processing apparatus 100 acquires, for example, captured image data obtained by capturing an image of the part used for manipulation as the second information. In addition, for example, the information processing apparatus 100 acquires data indicating a detection result of a pulse wave sensor from the first apparatus 300 as the first information and acquires information indicating the first apparatus.

The information processing apparatus 100 records the data indicating the detection result of the pulse wave sensor, acquired from the first apparatus 300, and the information indicating the first apparatus, for example, in table 2 shown in FIG. 3B.

The information processing apparatus 100 compares a value (an example of information based on the second information) indicating a pulse wave characteristic, which is acquired from a result of analysis of the acquired captured image data obtained by capturing an image of the part used for manipulation, with a value (an example of information based on the first information) indicating a pulse wave characteristic, which is represented by data indicating the detection result of the pulse wave sensor acquired from the first apparatus 300, to authenticate the user. For example, the value indicating the pulse wave characteristic may be obtained from a variation in the luminance of a moving image represented by the captured image data.

For example, the information processing apparatus 100 specifies a device ID corresponding to the value (an example of information based on the second information) indicating the pulse wave characteristic, which is acquired based on the captured image data obtained by capturing an image of the part used for manipulation, with reference to table 2 shown in FIG. 3B. The aforementioned process performed using table 2 corresponds to an example of the process of comparing the information based on the first information with the information based on the second information.

In addition, the information processing apparatus 100 specifies an account ID corresponding to the device ID with reference to table 1 shown in FIG. 3A. Here, a state in which the account ID has been specified using table 1 corresponds to a state in which user authentication related to the information processing method according to the present embodiment has been completed, for example. In the example of FIG. 8, for example, the manipulator X is authenticated when an account X corresponding to the manipulator X is specified as the account ID.

Furthermore, the information processing apparatus 100 may specify authority corresponding to the account ID, for example, with reference to table 3 shown in FIG. 3C.

In the first use case, the information processing apparatus 100 unlocks the safe, for example, when the input PIN is consistent with a registered number and user authentication related to the information processing method according to the present embodiment has been completed.

[3-2] Second Use Case: Multi-Key Safe

Figure 10:
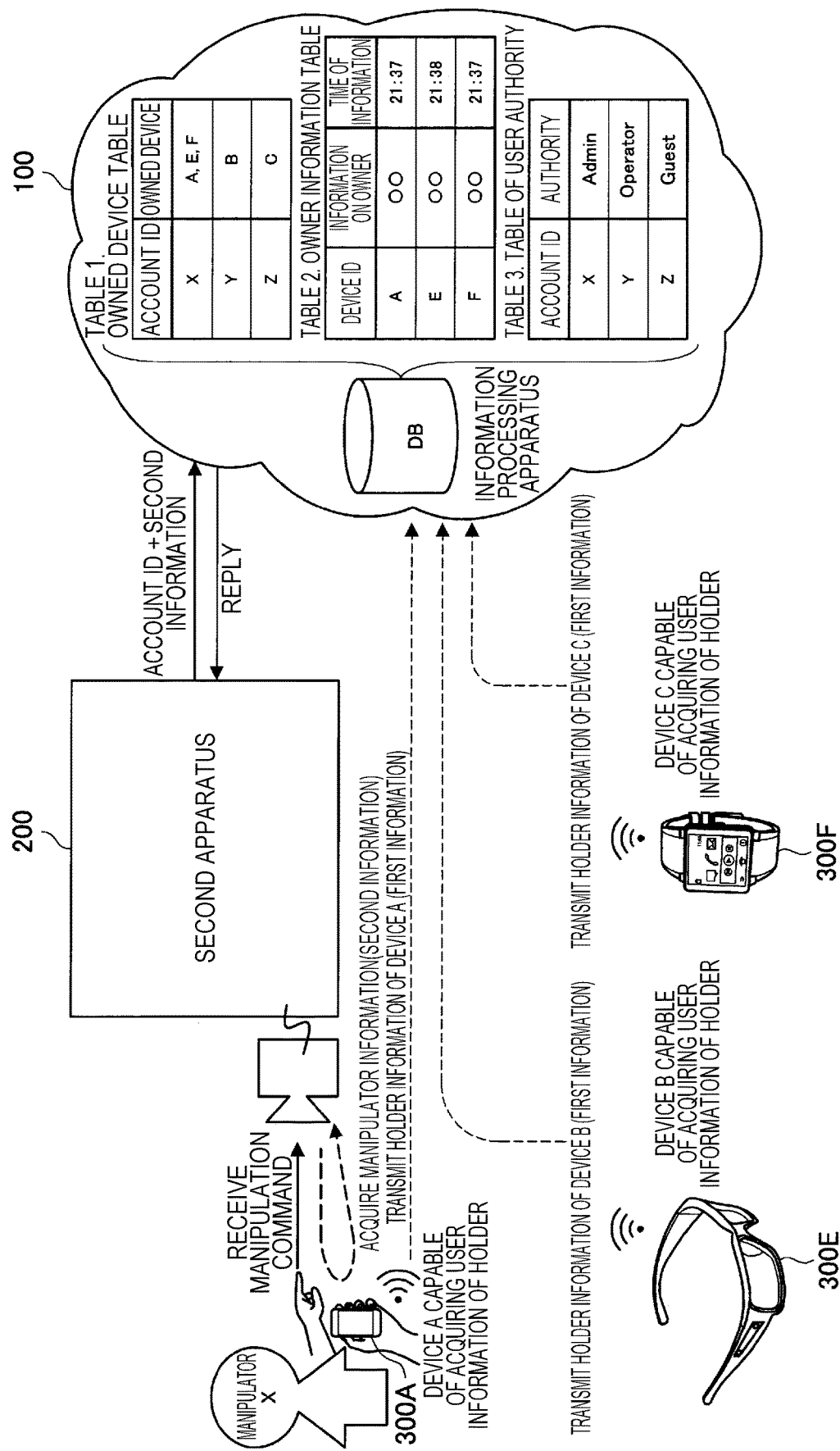
FIG. 10 is an explanatory diagram of the second use case to which the information processing method according to the present embodiment is applicable.

FIGS. 9 and 10 are explanatory diagrams of the second use case to which the information processing method according to the present embodiment is applicable and illustrate a use case applied to a multi-key safe. In the second use case, security is improved through user authentication according to the process related to the information processing method according to the present embodiment in addition to conventional security measures such as inputting a PIN and authentication using a fingerprint.

In the second use case, for example, an apparatus that manages unlocking of a door of a safe corresponds to the second apparatus 200. In addition, for example, an apparatus such as eyeglasses, a wrist watch or a smartphone corresponds to the first apparatus in the second use case. The information processing apparatus 100 performs communication with the second apparatus 200 and the first apparatus 300, for example, via a network (or directly).

An example of a process related to the information processing method according to the present embodiment in the second use case will be described with reference to FIG. 10. The case in which information based on the first information and information based on the second information are values indicating pulse wave characteristics shown in (A-1) above will be described below as an example.

When an image of a hand of a manipulator X who inputs a PIN is captured by an image sensor configured of an imaging device or the like, the information processing apparatus 100 acquires, for example, captured image data obtained by capturing an image of the part used for manipulation as the second information from the second apparatus 200. In addition, for example, the information processing apparatus 100 acquires data indicating detection results of pulse wave sensors as the first information from the first apparatuses 300A, 300E and 300F, and acquires information indicating the first apparatuses.

The information processing apparatus 100 records the data indicating the detection results of the pulse wave sensors acquired from the first apparatuses 300A, 300E and 300F, and the information indicating the first apparatuses, for example, in table 2 shown in FIG. 10.

The information processing apparatus 100 compares a value (an example of information based on the second information) indicating a pulse wave characteristic acquired from a result of analysis of the captured image data obtained by capturing an image of the part used for manipulation, acquired from the second apparatus 200, with values (an example of information based on the first information) indicating pulse wave characteristics represented by the data indicating the detection results of the pulse wave sensors, acquired from the first apparatuses 300A, 300E and 300F to authenticate the user.

For example, the information processing apparatus 100 specifies a device ID corresponding to the value (an example of information based on the second information) indicating the pulse wave characteristic, which is acquired based on the captured image data obtained by capturing an image of the part used for manipulation, with reference to table 2 shown in FIG. 10. The aforementioned process performed using table 2 corresponds to an example of the process of comparing the information based on the first information with the information based on the second information.

In addition, the information processing apparatus 100 specifies an account ID corresponding to the device ID with reference to table 1 shown in FIG. 10. Here, a state in which the account ID has been specified using table 1 corresponds to a state in which user authentication related to the information processing method according to the present embodiment has been completed, for example.

The information processing apparatus 100 specifies an account ID, for example, when one of device IDs associated with account IDs in table 1 corresponds to the device ID specified based on the value (an example of the information based on the second information) indicating the pulse wave characteristic. In addition, the information processing apparatus 100 may specify an account ID, for example, when equal to or more than a set number of device IDs among device IDs associated with account IDs in table 1 correspond to the device ID specified based on the value (an example of the information based on the second information) indicating the pulse wave characteristic. For example, when all device IDs associated with account IDs in table 1 correspond to the device ID specified based on the value (an example of the information based on the second information) indicating the pulse wave characteristic, an account ID is specified, and thus security can be further improved.

In the example of FIG. 10, for example, the manipulator X is authenticated when an account X corresponding to the manipulator X is specified as the account ID.

Furthermore, the information processing apparatus 100 may specify authority corresponding to the account ID, for example, with reference to table 3 shown in FIG. 10.

In the second use case, the information processing apparatus 100 causes the second apparatus 200 to unlock the safe, for example, when the input PIN is consistent with a registered number or a fingerprint is consistent with a registered fingerprint, and user authentication related to the information processing method according to the present embodiment has been completed.

[3-3] Third Use Case: Manipulation-Free Authentication Terminal System

Figure 11:
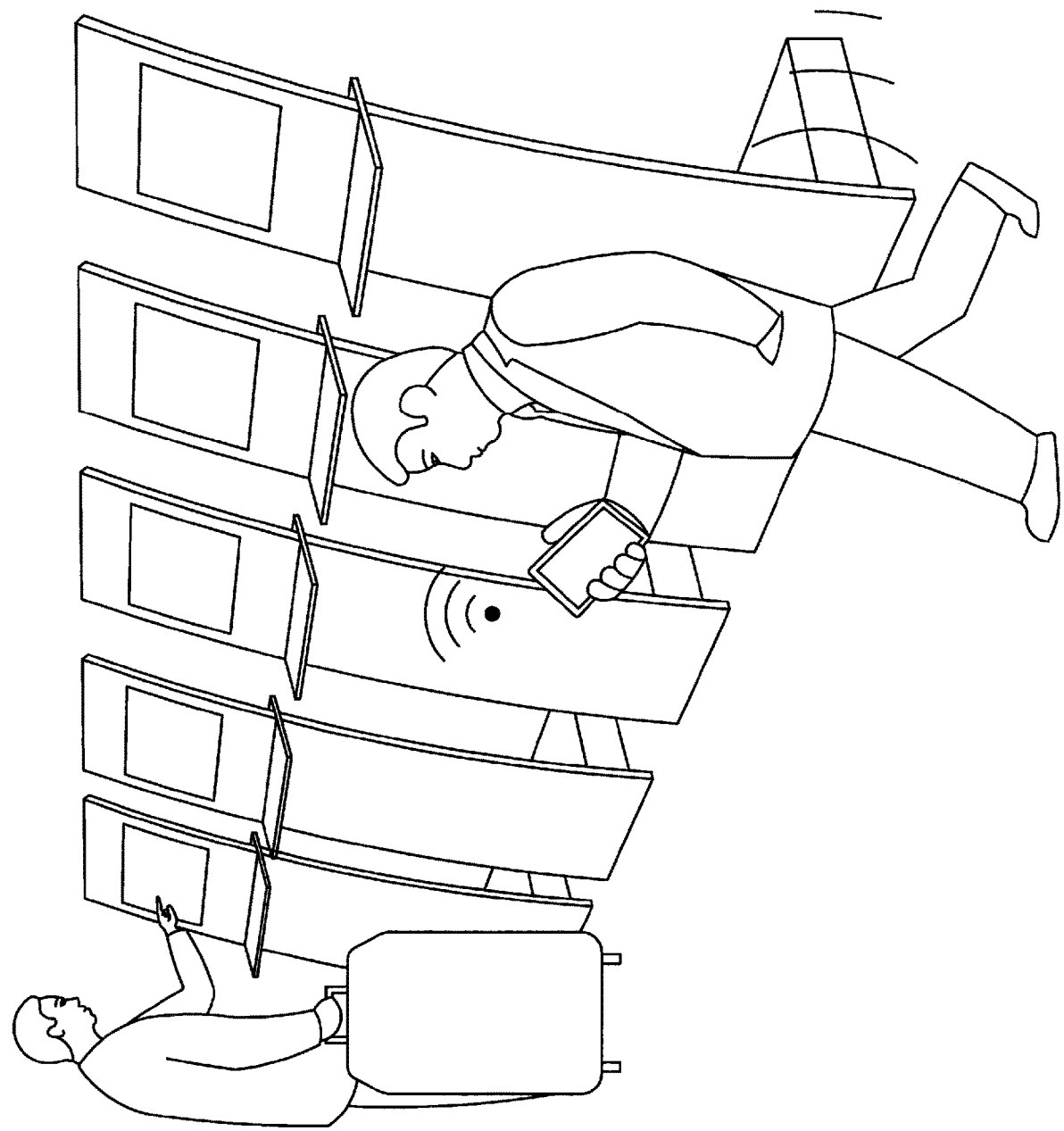
FIG. 11 is an explanatory diagram of a third use case to which the information processing method according to the present embodiment is applicable.
Figure 12:
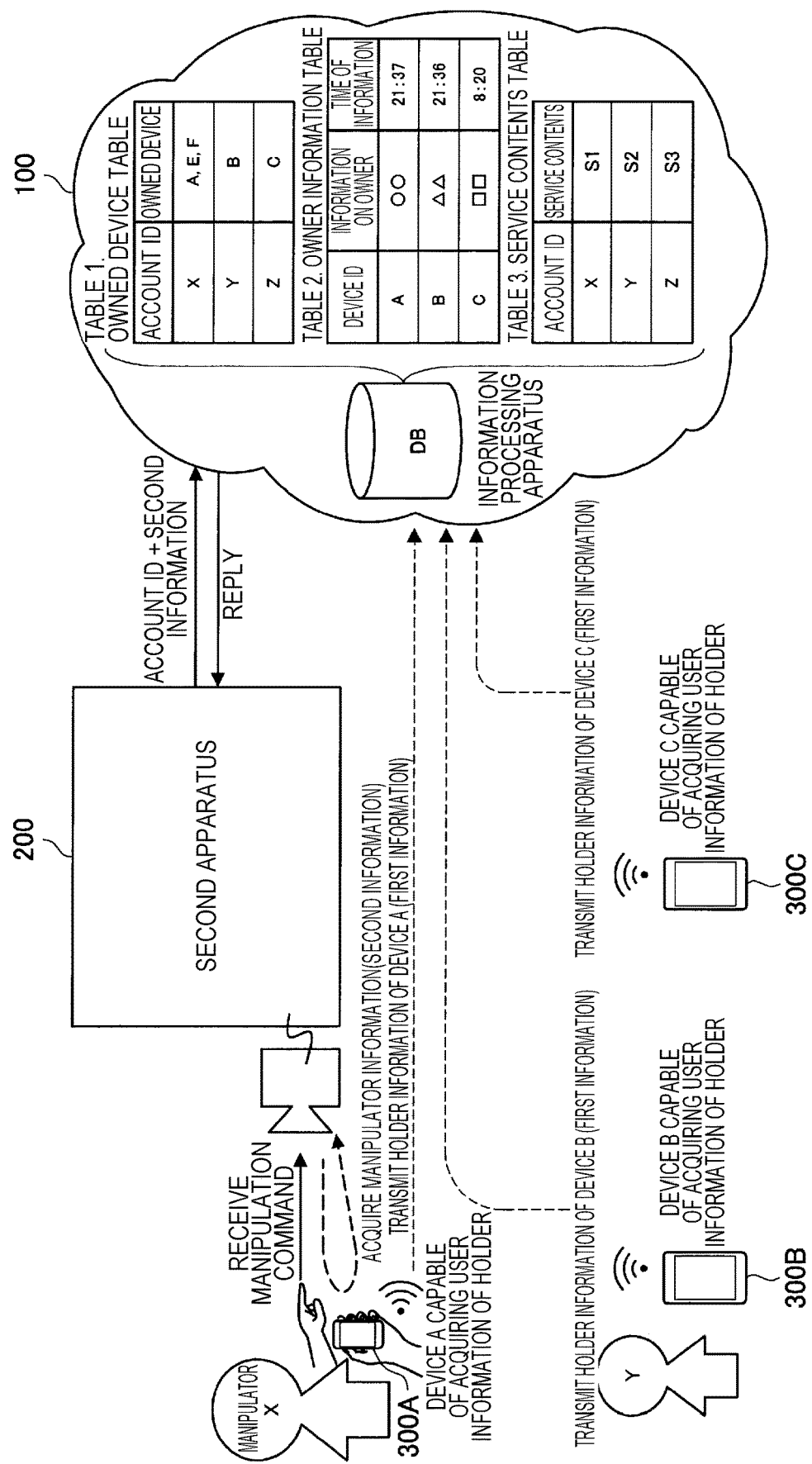
FIG. 12 is an explanatory diagram of the third use case to which the information processing method according to the present embodiment is applicable.

FIGS. 11 and 12 are explanatory diagrams of the third use case to which the information processing method according to the present embodiment is applicable and illustrate a use case applied to a manipulation-free authentication terminal system, which is installed in a public space such as an airport. In the third use case, a registered user permitted to use a manipulation-free authentication terminal (an example of the second apparatus 200) can be authenticated without performing a manipulation related to authentication of the manipulation-free authentication terminal to use the manipulation-free authentication terminal.

In the third use case, for example, the manipulation-free authentication terminal corresponds to the second apparatus 200. In addition, for example, an apparatus such as eyeglasses, a wrist watch or a smartphone corresponds to the first apparatus 300 in the third use case. The information processing apparatus 100 performs communication with the second apparatus 200 and the first apparatus 300, for example, via a network (or directly).

An example of a process related to the information processing method according to the present embodiment in the third use case will be described with reference to FIG. 12. The case in which information based on the first information and information based on the second information are values indicating pulse wave characteristics shown in (A-1) above will be described below as an example.

For example, the second apparatus 200 transmits a signal including a command for causing a device ID to be transmitted through wireless communication and acquires the device ID transmitted in response to the command from an apparatus located in the coverage area of the wireless communication. Then, the second apparatus 200 transmits the acquired device ID to the information processing apparatus 100. For example, the device ID transmitted from the second apparatus 200 corresponds to a candidate device ID of an apparatus that is likely to be worn on the body of a manipulator who manipulates the second apparatus 200.

For example, the information processing apparatus 100 specifies a record including a device ID consistent with the candidate device ID acquired from the second apparatus 200 with reference to table 1 of FIG. 12. As the record is specified based on the candidate device ID, records of account IDs that do not correspond to the candidate device ID can be excluded from processing targets even when the number of records of table 1 increases, for example, and thus a processing time such as a time required to search table 1 can be reduced.

Meanwhile, the process related to the candidate device ID may not be performed in one or both of the information processing apparatus 100 and the second apparatus 200 in the third use case.

When an image of a hand of a manipulator X who intends to manipulate the manipulation-free authentication terminal (second apparatus 200) is captured by an image sensor configured of an imaging device or the like, for example, the information processing apparatus 100 acquires captured image data obtained by capturing an image of the part used for manipulation as the second information. In addition, for example, the information processing apparatus 100 acquires values indicating detection results of pulse wave sensors as the first information from the first apparatuses 300A, 300B and 300C and acquires information indicating the first apparatuses.

The information processing apparatus 100 records data indicating the detection results of the pulse wave sensors, acquired from the first apparatuses 300A, 300E and 300F and the information indicating the first apparatus, for example, in table 2 shown in FIG. 12.

The information processing apparatus 100 compares a value (an example of information based on the second information) indicating a pulse wave characteristic acquired from a result of analysis of the captured image data obtained by capturing an image of the part used for manipulation, acquired from the second apparatus 200, with values (an example of information based on the first information) indicating pulse wave characteristics represented by the data indicating the detection results of the pulse wave sensors, acquired from the first apparatuses 300A, 300E and 300F to authenticate the user.

For example, the information processing apparatus 100 specifies a device ID corresponding to the value (an example of the information based on the second information) indicating the pulse wave characteristic acquired based on the captured image data obtained by capturing an image of the part used for manipulation with reference to table 2 shown in FIG. 12. The process performed using table 2 corresponds to an example of the process of comparing the information based on the first information with the information based on the second information.

In addition, the information processing apparatus 100 specifies an account ID corresponding to the device ID with reference to table 1 shown in FIG. 12 as in the second use case described in [3-2]. Here, for example, a state in which the account ID has been specified using table 1 corresponds to a state in which user authentication related to the information processing apparatus according to the present embodiment has been completed.

In the example of FIG. 12, for example, the manipulator X is authenticated when an account X corresponding to the manipulator X is specified as the account ID.

In addition, the information processing apparatus 100 specifies a service corresponding to the account ID, for example, with reference to table 3 shown in FIG. 12. Then, the information processing apparatus 100 causes the manipulation-free authentication terminal, which is the second apparatus 200, to perform a process related to provision of the specified service (an example of a process corresponding to the authenticated user). As the process related to provision of the service in the third use case, for example, mirroring content displayed on a display screen of a smartphone gripped by a hand of the authenticated manipulator X, providing content corresponding to the service provided to the authentication manipulator X, or the like may be exemplified.

In the third use case, the information processing apparatus 100 performs user authentication related to the information processing method according to the present embodiment. Accordingly, the user who intends to use the manipulation-free authentication terminal can receive a service using the manipulation-free authentication terminal by merely standing in front of the manipulation-free authentication terminal (for example, by merely standing at a position at which an image of the part used for manipulation can be captured) with the first apparatus 300 worn on the body of the user, for example.

Figure 13:
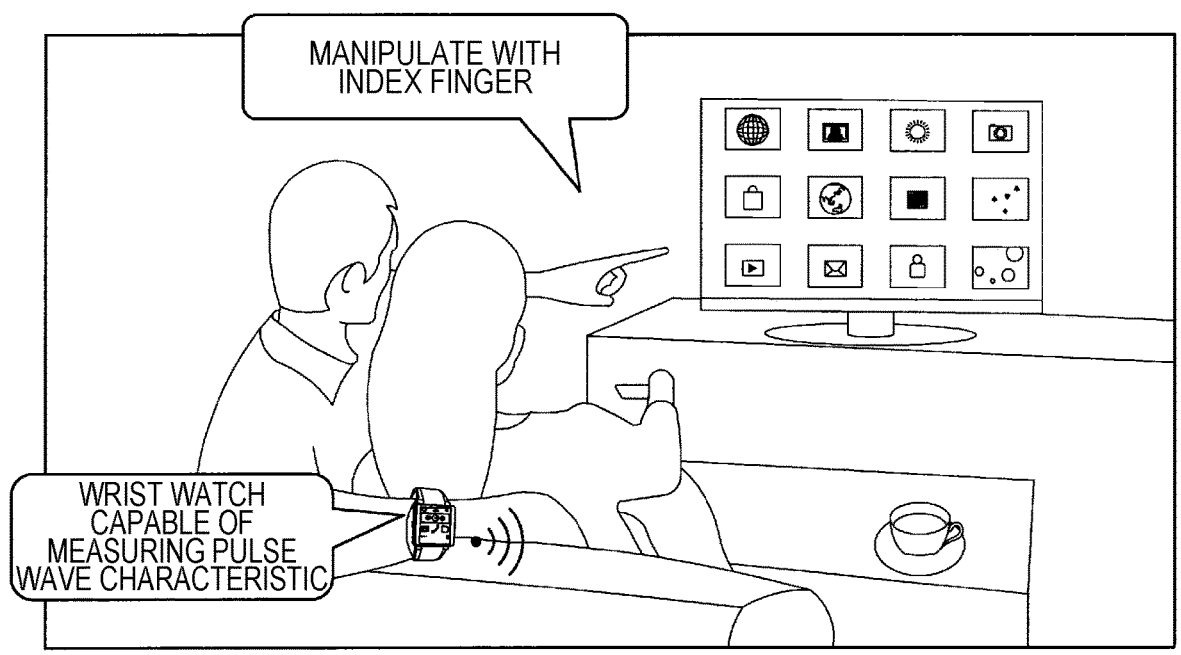
FIG. 13 is an explanatory diagram of a fourth use case to which the information processing method according to the present embodiment is applicable.
Figure 14:
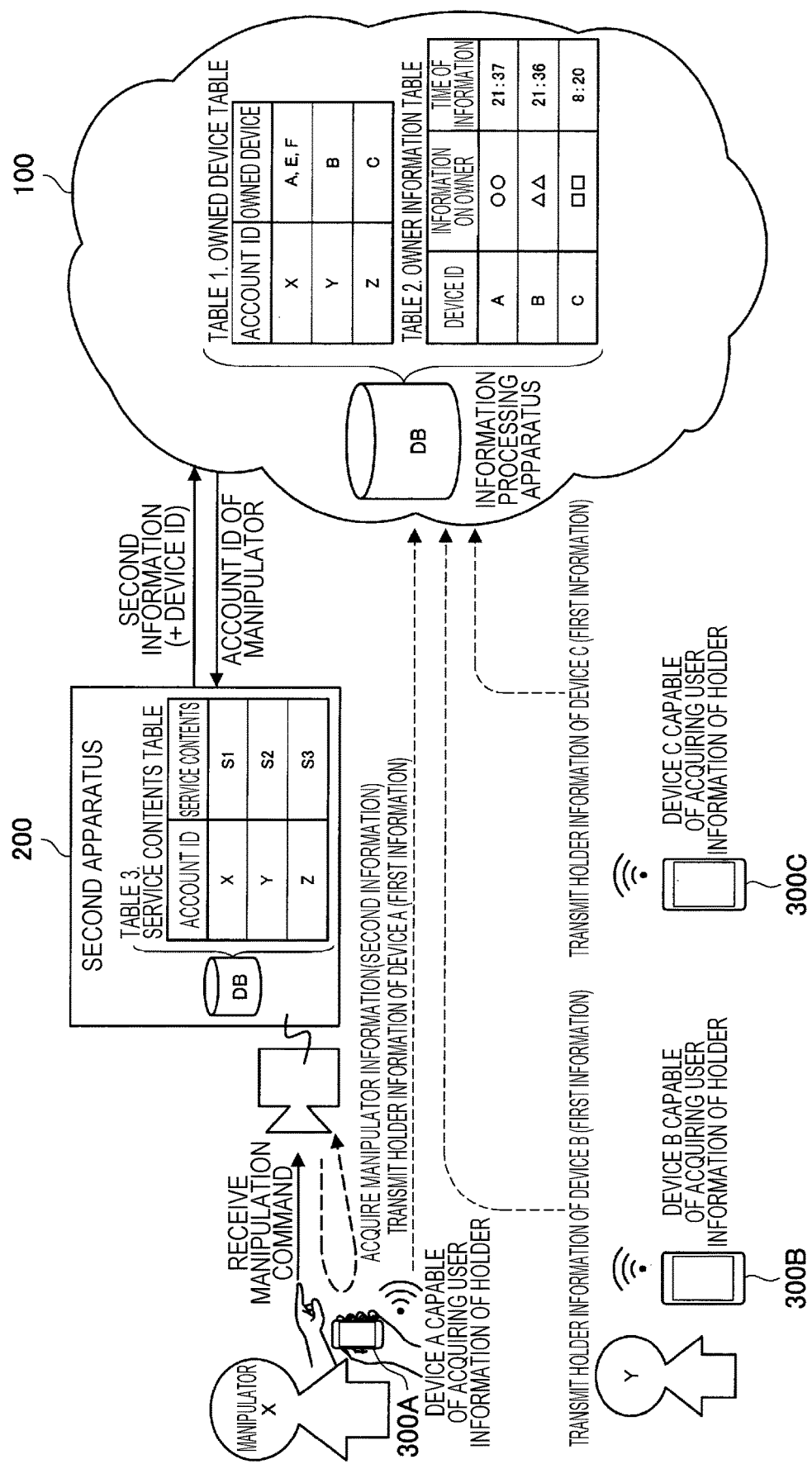
FIG. 14 is an explanatory diagram of the fourth use case to which the information processing method according to the present embodiment is applicable.

[3-4] Fourth Use Case: Manipulation-Free Authentication Information Home Electric Appliance System FIGS. 13 and 14 are explanatory diagrams of the fourth use case to which the information processing method according to the present embodiment is applicable and illustrate a use case applied to a manipulation-free authentication information home appliance system installed in a house and the like. In the fourth use case, a registered user permitted to use a manipulation-free authentication home electric appliance apparatus (an example of the second apparatus 200) can be authenticated without performing a manipulation related to authentication of the manipulation-free authentication home appliance apparatus to use the manipulation-free authentication home appliance apparatus.

In the fourth use case, for example, the manipulation-free authentication home appliance apparatus corresponds to the second apparatus 200. In addition, for example, an apparatus such as eyeglasses, a wrist watch or a smartphone corresponds to the first apparatus 300 in the fourth use case. The information processing apparatus 100 performs communication with the second apparatus 200 and the first apparatus 300, for example, via a network (or directly).

An example of a process related to the information processing method according to the present embodiment in the fourth use case will be described with reference to FIG. 14. The case in which information based on the first information and information based on the second information are values indicating pulse wave characteristics shown in (A-1) above will be described below as an example.

When an image of a hand of a manipulator X who inputs a PIN is captured by an image sensor configured of an imaging device or the like, for example, the information processing apparatus 100 acquires captured image data obtained by capturing an image of the part used for manipulation as the second information from the second apparatus 200. In addition, for example, the information processing apparatus 100 acquires data indicating detection results of pulse wave sensors as the first information from the first apparatuses 300A, 300B and 300C and acquires information indicating the first apparatuses.

The information processing apparatus 100 records data indicating the detection results of the pulse wave sensors, acquired from the first apparatuses 300A, 300B and 300C and the information indicating the first apparatus, for example, in table 2 shown in FIG. 14.

The information processing apparatus 100 compares a value (an example of information based on the second information) indicating a pulse wave characteristic acquired from a result of analysis of the captured image data obtained by capturing an image of the part (e.g., a hand part performing a gesture manipulation, or the like) used for manipulation, acquired from the second apparatus 200, with values (an example of information based on the first information) indicating pulse wave characteristics represented by the data indicating the detection results of the pulse wave sensors acquired from the first apparatuses 300A, 300B and 300C to authenticate the user.

For example, the information processing apparatus 100 specifies a device ID corresponding to the value (an example of the information based on the second information) indicating the pulse wave characteristic acquired based on the captured image data obtained by capturing an image of the part used for manipulation with reference to table 2 shown in FIG. 14. The process performed using table 2 corresponds to an example of the process of comparing the information based on the first information with the information based on the second information.

In addition, the information processing apparatus 100 specifies an account ID corresponding to the device ID, for example, with reference to table 1 shown in FIG. 14 as in the second use case described in [3-2]. Here, for example, a state in which the account ID has been specified using table 1 corresponds to a state in which user authentication related to the information processing method according to the present embodiment has been completed.

In the example of FIG. 14, for example, the manipulator X is authenticated when an account X corresponding to the manipulator X is specified as the account ID.

The information processing apparatus 100 causes the manipulation-free authentication home appliance apparatus, which is the second apparatus 200, to perform a process corresponding to the specified account ID (an example of a process corresponding to the authenticated user). As the process corresponding to the account ID in the third use case, for example, a process of providing a unique UI of the manipulator X, or the like, such as displaying a folder of the authenticated manipulator X on a display screen, may be exemplified. In addition, when the authenticated manipulator X points to an object related to the UI on the display screen with the index finger and performs a predetermined gesture operation such as masking a fist, for example, the object is selected (or decided) in the fourth use case.

In the fourth use case, the information processing apparatus 100 performs user authentication related to the information processing method according to the present embodiment. Accordingly, a user who intends to use the manipulation-free authentication home appliance apparatus can use the manipulation-free authentication home appliance apparatus in his or her own manipulation environment, for example, by merely being in front of the manipulation-free authentication home appliance apparatus (e.g., being at a position at which an image of the part used for manipulation can be captured) in a state in which the first apparatus 300 is worn on his or her body without registering information of his or her face (an example of bio-information).

[3-5] Fifth Use Case: Voice Agent

FIGS. 15A and 15B are explanatory diagrams of the fifth use case to which the information processing method according to the present embodiment is applicable and illustrates a use case applied to an agent that can manipulate a device using a voice.

In the fifth use case, an agent robot that receives a device manipulation command with a voice command and controls a device operation, illustrated in FIG. 15B, corresponds to the second apparatus 200. In addition, a smartphone illustrated in FIG. 15A corresponds to the first apparatus 300 in the fifth use case. The information processing apparatus 100 performs communication with the second apparatus 200 and the first apparatus 300, for example, via a network (or directly).

An example of a process related to the information processing method according to the present embodiment in the fifth use case will be described with reference to FIGS. 15A and 15B. A case in which information based on the first information and information based on the second information are information indicating contents of previous conversation shown in (C-2) above will be described below as an example.

For example, the first apparatus 300 continuously detects voice using a voice detection sensor. The information processing apparatus 100 acquires, for example, data indicating a detection result of the voice detection sensor as the first information from the first apparatus 300.

In addition, the second apparatus 200 continuously detects voice using a voice detection sensor. For example, the information processing apparatus 100 acquires data indicating a detection result of the voice detection sensor as the second information from the second apparatus 200.

The information processing apparatus 100 compares a phrase (an example of information based on the second information) obtained by analyzing the data (the second information) indicating the detection result of the voice detection sensor, acquired from the second apparatus 200, with an item (an example of information based on the first information) estimated to arouse a user's interest, which is obtained by analyzing the data (the first information) indicating the detection result of the voice detection sensor acquired from the first apparatus 300.

Then, the information processing apparatus 100 causes the second apparatus 200 to perform a process corresponding to the phrase (an example of the information based on the second information) when it is determined that the phrase (an example of the information based on the second information) is a phrase corresponding to the item (an example of information based on the first information) estimated to arouse the user's interest. For example, in FIGS. 15A and 15B, the agent robot (the second apparatus 200) replies to the user's speech indicating that the user wants to watch a soccer program as the process corresponding to the phrase (an example of the information based on the second information) as shown in FIG. 15B. Then, the agent robot (the second apparatus 200) causes a TV receiver to display the soccer program, as shown in FIG. 15A, for example.

[3-6] Sixth Use Case: Car that is Not Operated when Key is Stolen

Figure 16:
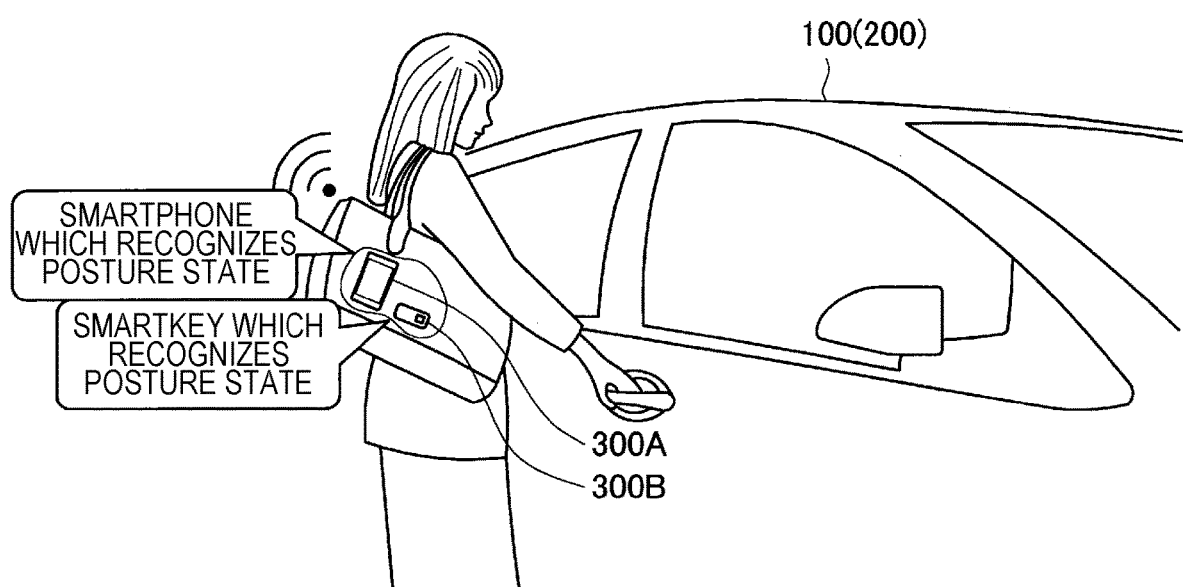

FIG. 16 is an explanatory diagram of the sixth use case to which the information processing method according to the present embodiment is applicable and illustrates a use case applied to a car that is not operated when its key is stolen.

In the sixth use case, the car corresponds to the information processing apparatus 100 and the second apparatus 200. In addition, for example, an apparatus such as eyeglasses, a wrist watch, a smartphone or a car key (e.g., a smartkey shown in FIG. 16) corresponds to the first apparatus 300 in the sixth use case.

The case in which information based on the first information and information based on the second information are values indicating pulse wave characteristics shown in (A-1) above will be described below as an example.

When an image of a manipulator's hand gripping a door handle of the car is captured by an image sensor configured of an imaging device or the like, the information processing apparatus 100 acquires, for example, captured image data obtained by capturing an image of the part used for manipulation as the second information. In addition, when a sensor capable of acquiring a value indicating a pulse wave characteristic through a touch is attached to the door handle, the information processing apparatus 100 may acquire, for example, data indicating a value indicating a pulse wave characteristic, which is a detection result of the sensor, as the second information.

Furthermore, for example, the information processing apparatus 100 acquires data indicating detection results of pulse wave sensors as the first information from the first apparatuses 300A and 300B. In addition, the information processing apparatus 100 may acquire, for example, information indicating posture states (e.g., data indicating walking, standing, sitting or the like, or data indicating a detection value of a gyro sensor or an acceleration sensor) as the first information from the first apparatuses 300A and 300B.

The information processing apparatus 100 records the data indicating the detection results of the pulse wave sensors acquired from the first apparatuses 300A and 300B and information indicating the first apparatuses, for example, in table 2 shown in FIG. 3B.

The information processing apparatus 100 compares a value (an example of information based on the second information) indicating a pulse wave characteristic obtained from a result of analysis of the acquired captured image data obtained by capturing an image of the part used for manipulation (e.g., the hand part gripping the door handle, or the like) with values (an example of information based on the first information) indicating pulse wave characteristics represented by the data indicating the detection results of the pulse wave sensors, acquired from the first apparatuses 300A and 300B, to authenticate the user.

When the second information is the captured image data obtained by capturing an image of the part used for manipulation, for example, the information processing apparatus 100 specifies a device ID corresponding to the value (an example of the information based on the second information) indicating the pulse wave characteristic acquired based on the captured image data obtained by capturing an image of the part used for manipulation with reference to table 2 shown in FIG. 3B. In addition, when the second information is data indicating a value representing a pulse wave characteristic, for example, the information processing apparatus 100 specifies a device ID corresponding to a value (an example of the information based on the second information) indicating a pulse wave characteristic represented by data indicating the value representing the pulse wave characteristic with reference to table 2 shown in FIG. 3B. The process performed using table 2 corresponds to an example of the process of comparing the information based on the first information with the information based on the second information.

In addition, the information processing apparatus 100 specifies an account ID corresponding to the device ID, for example, with reference to a table such as table 1 shown in FIG. 3A. In the sixth use case, for example, account IDs and a plurality of device IDs are associated in the table, and an account ID is specified when two or more of the associated device IDs are consistent with the device ID specified based on the value indicating the pulse wave characteristic (an example of the information based on the second information)

Here, a state in which the account ID has been specified using the table corresponds to a state in which user authentication related to the information processing method according to the present embodiment has been completed, for example.

Accordingly, in the sixth use case, even if the key of the car is stolen, the car is not operated using the stolen key because authentication is not completed only using the car key (e.g., the smartkey shown in FIG. 16), for example.

Meanwhile, authentication timing in the sixth use case is not limited to the aforementioned example. For example, authentication may be performed at any timing, such as a case in which the manipulator presses an engine switch while stepping on a brake, in the sixth use case.

Furthermore, when authentication is performed in which the manipulator presses the engine switch while stepping on the brake in the aforementioned case, the information processing apparatus 100 may estimate the posture of the manipulator on the basis of the information indicating a posture state, acquired as the first information, and further perform authentication using the estimated posture. For example, when authentication is performed in which the manipulator presses the engine switch while stepping on the brake in the aforementioned case, the information processing apparatus 100 authenticates the manipulator when the estimated posture of the manipulator is seating.

As use cases to which the information processing method according to the present embodiment is applicable, for example, the first use case described in [3-1] above to the sixth use case described in [3-6] above may be exemplified. However, of course, use cases to which the information processing method according to the present embodiment is applicable are not limited from the first use case described in [3-1] above to the sixth use case described in [3-6] above.

(Information Processing Apparatus According to Present Embodiment)

Next, an example of a configuration of the information processing apparatus according to the present embodiment, which can perform the above-described processes related to the information processing method according to the present embodiment, will be described.

Figure 17:
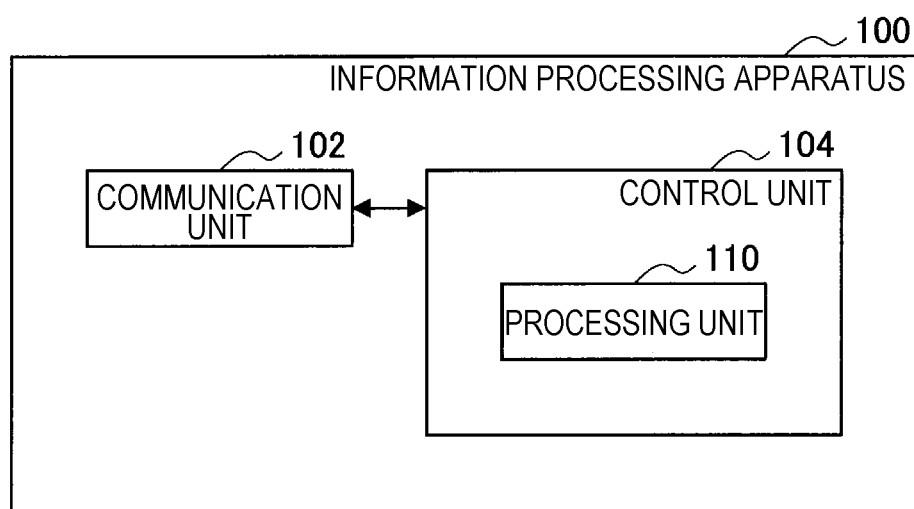

FIG. 17 is a block diagram illustrating an example of a configuration of the information processing apparatus 100 according to the present embodiment. For example, the information processing apparatus 100 includes a communication unit 102 and a control unit 104.

In addition, the information processing apparatus 100 may include, for example, a read only memory (ROM) (not shown), a random access memory (RAM) (not shown), a storage unit (not shown), a manipulation unit (not shown) which can be manipulated by a user, a display unit (not shown) for displaying various screens on a display screen, and the like. For example, the information processing apparatus 100 connects the aforementioned components through a bus which is a data transmission path.

The ROM (not shown) stores control data such as programs and operation parameters used by the control unit 104. The RAM (not shown) temporarily stores programs executed by the control unit 104, and the like.

The storage unit (not shown) is a storage means included in the information processing apparatus 100 and stores, for example, data related to the information processing method according to the present embodiment, such as "data in which the first information or information based on the first information and information indicating the first apparatus are associated and recorded," and various types of data such as various applications. Here, as the storage unit (not shown), for example, a magnetic recording medium such as a hard disk, a nonvolatile memory such as a flash memory, or the like may be exemplified. In addition, the storage unit (not shown) may be attachable/detachable to/from the information processing apparatus 100.

As the manipulation unit (not shown), a manipulation input device, which will be described below, may be exemplified. Further, as the display unit (not shown), a display device, which will be described below, may be exemplified.

[Hardware Configuration Example of Information Processing Apparatus 100]

Figure 18:
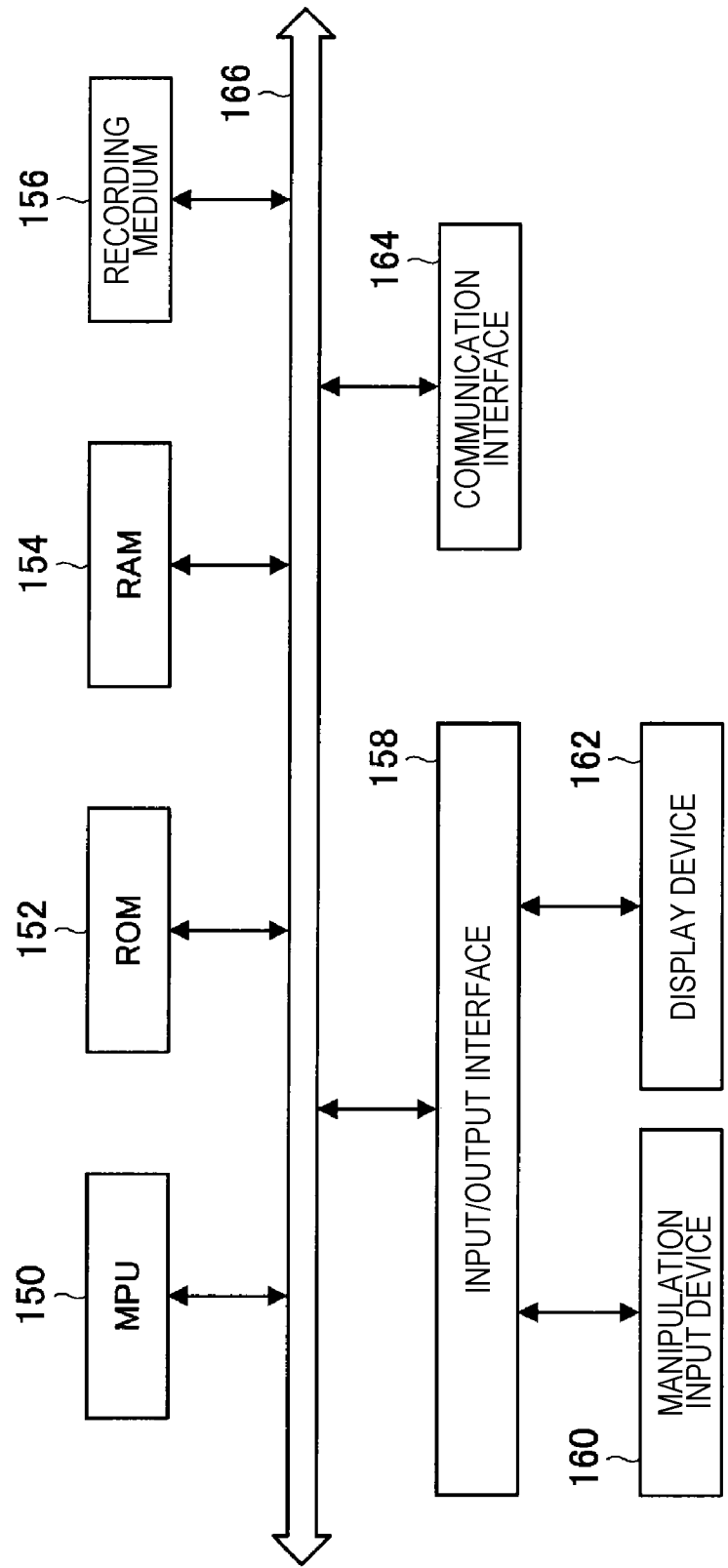

FIG. 18 is an explanatory diagram of an example of a hardware configuration of the information processing apparatus 100 according to the present embodiment. For example, the information processing apparatus 100 includes an MPU 150, a ROM 152, a RAM 154, a recording medium 156, an input/output interface 158, a manipulation input device 160, a display device 162, and a communication interface 164. In addition, the information processing apparatus 100 connects the components, for example, using a bus 166 which is a data transmission path.

For example, the MPU 150 is composed of one or more processors, which are configured of an operation circuit such as a micro processing unit (MPU), various processing circuits and the like and functions as the control unit 104 for controlling the entire information processing apparatus 100. In addition, the MPU 150 serves as, for example, a processing unit 110, which will be described below, in the information processing apparatus 100. Meanwhile, the processing unit 110 may be composed of a dedicated (or general-purpose) circuit (e.g., a processor or the like) which can realize processes of the components.

The ROM 152 stores control data such as programs and operation parameters used by the MPU 150, and the like. The RAM 154 temporarily stores programs executed by the MPU, and the like, for example.

The recording medium 156 functions as a storage unit (not shown) and stores, for example, data related to the information processing method according to the present embodiment, such as "data in which the first information or information based on the first information and information indicating the first apparatus are associated and recorded," and various types of data such as various applications. Here, as the recording medium 156, for example, a magnetic recording medium such as a hard disk, a nonvolatile memory such as a flash memory, or the like may be exemplified. In addition, the recording medium 156 may be attachable/detachable to/from the information processing apparatus 100.

The input/output interface 158 connects, for example, the manipulation input device 160 and the display device 162. The manipulation input device 160 functions as a manipulation unit (not shown) and the display device 162 functions as a display unit (not shown). Here, as the input/output interface 158, for example, a Universal Serial Bus (USB) terminal, a Digital Visual Interface (DVI) terminal, a High-Definition Multimedia Interface (HDMI) (registered trademark) terminal, various processing circuits, or the like may be exemplified.

Furthermore, for example, the manipulation input device 160 is installed on the information processing apparatus 100 and connected to the input/output interface 158 inside the information processing apparatus 100. As the manipulation input device 160, for example, a button, a direction key, a rotary selector such as a jog dial, or a combination thereof, or the like may be exemplified.

In addition, for example, the display device 162 is installed on the information processing apparatus 100 and connected to the input/output interface 158 inside the information processing apparatus 100. As the display device 162, for example, a liquid crystal display, an organic electroluminescence display, an organic light emitting diode (OLED) display or the like may be exemplified.

Of course, the input/output interface 158 may be connected to external devices such as an external manipulation input device (e.g., a keyboard, a mouse or the like) and an external display device, which are external apparatuses of the information processing apparatus 100. Further, the display device 162 may be a device capable of performing display and being manipulated by a user, for example, a touch panel or the like.

The communication interface 164 is a communication means included in the information processing apparatus 100 and functions as the communication unit 102 for performing communication with external apparatuses such as the second apparatus 200 and the first apparatus 300 via a network (or directly) in a wireless or wired manner.

Here, as the communication interface 164, for example, a communication antenna and a radio frequency (RF) circuit (wireless communication), an IEEE 802.15.1 port and a transceiving circuit (wireless communication), an IEEE 802.11 port and a transceiving circuit (wireless communication), a local area network (LAN) terminal and a transceiving circuit (wired communication), or the like may be exemplified. As a network according to the present embodiment, for example, a wired network such as a local area network (LAN) or a wide area network (WAN), a wireless network such as a wireless local area network (WLAN), the Internet using a communication protocol such as a transmission control protocol/Internet protocol (TCP/IP), or the like may be exemplified.

The information processing apparatus 100 performs processes related to the information processing method according to the present embodiment, for example, through the configuration shown in FIG. 18. Meanwhile, the hardware configuration of the information processing apparatus 100 according to the present embodiment is not limited to the configuration shown in FIG. 18.

For example, when the information processing apparatus 100 performs communication with an external apparatus or the like via a connected external communication device, the information processing apparatus 100 may not include the communication interface 164. Furthermore, the communication interface 164 may have a configuration capable of performing communication with one or more external apparatuses according to a plurality of communication schemes.

In addition, the information processing apparatus 100 may have, for example, a configuration that does not include the recording medium 156, the manipulation input device 160 and the display device 162.

Furthermore, the configuration shown in FIG. 18 (or a configuration related to a modified example) may be realized, for example, using one or more integrated circuits (ICs).

An example of the configuration of the information processing apparatus 100 will be described with reference to FIG. 17 again. The communication unit 102 is a communication means included in the information processing apparatus 100 and performs communication with external apparatuses such as the second apparatus 200 and the first apparatus 300 via a network (or directly) in a wireless or wired manner. In addition, communication of the communication unit 102 is controlled, for example, by the control unit 104.

Here, although a communication antenna and an RF circuit, a LAN terminal and a transceiving circuit, or the like, for example, may be exemplified as the communication unit 102, the configuration of the communication unit 102 is not limited thereto. For example, the communication unit 102 may have a configuration corresponding to any standard that enables communication, such as a USB terminal and a transceiving circuit, or any configuration capable of performing communication with an external apparatus via a network. In addition, the communication unit 102 may have a configuration capable of performing communication with one or more external apparatuses through a plurality of communication schemes.

The control unit 104 is configured, for example, of an MPU or the like and serves to control the entire information processing apparatus 100. In addition, the control unit 104 includes the processing unit 110, for example, and serves a leading role in performing processes related to the information processing method according to the present embodiment.

The processing unit 110 serves a leading role in performing processes related to the information processing method according to the present embodiment, and compares information based on the second information, which is based on the second information acquired from the second apparatus 200, with information based on the first information, which is based on the first information acquired from the first apparatus 300, to perform a predetermined process.

For example, the processing unit 110 compares the information based on the first information and the information based on the second information, which correspond to each other, as shown in (A) to (C) above. For example, when the information based on the first information and the information based on the second information are the data indicating values representing pulse wave characteristics, shown in (A-1) above, the processing unit 110 compares a value (an example of a value indicated by the information based on the second information) of a pulse wave specified from a captured image with a value (an example of a value indicated by the information based on the first information) of a pulse wave indicated by a detection result of a pulse wave sensor. In addition, when the information based on the first information and the information based on the second information are the information indicating a shape of a part used for manipulation, shown in (A-2) above, for example, the processing unit 110 compares a myoelectric value (an example of a value indicated by the information based on the second information) specified from a captured image with a myoelectric value (an example of a value indicated by the information based on the first information) indicated by a detection result of a myoelectric sensor.

Furthermore, for example, the processing unit 110 performs any process that can be performed based on a comparison between the information based on the first information (or the first information) and the information based on the second information (or the second information), for example, an authentication process, a process related to execution control of a process corresponding to an authenticated user, or the like, as a predetermined process. In addition, the processing unit 110 may switch predetermined processes, for example, on the basis of "whether a user corresponding to the first information is identical to a user corresponding to the second information" or the like.

For example, the control unit 104 plays a leading role in performing processes related to the information processing method according to the present embodiment by including the processing unit 110.

The information processing apparatus 100 performs processes related to the information processing method according to the present embodiment, for example, through the configuration shown in FIG. 17.

Accordingly, the information processing apparatus 100 can improve user convenience, for example, according to the configuration shown in FIG. 17.

In addition, the information processing apparatus 100 can achieve effects obtained when the above-described processes related to the information processing method according to the present embodiment are performed, for example, through the configuration shown in FIG. 17.

Meanwhile, the configuration of the information processing apparatus according to the present embodiment is not limited to the configuration shown in FIG. 17.

For example, the information processing apparatus according to the present embodiment may include the processing unit 110 shown in FIG. 17 separately from the control unit 104 (e.g., realize separate processing circuits).

In addition, when communication with an external apparatus is performed via an external communication device having the same function and configuration as those of the communication unit 102, for example, the information processing apparatus according to the present embodiment may not include the communication unit 102.

Although the information processing apparatus has been described as the present embodiment, the present embodiment is not limited to such a form. For example, the present embodiment is applicable various devices which can perform processes related to the information processing method according to the present embodiment, such as computers such as personal computers (PC) and servers. Furthermore, the present embodiment may be applied to, for example, processing ICs which can be integrated into the aforementioned devices.

Furthermore, as described in the aforementioned use cases, the information processing apparatus according to the present embodiment may be an apparatus integrated with the first apparatus according to the present embodiment depending on use cases to which the information processing method according to the present embodiment is applied.

In addition, the information processing apparatus according to the present embodiment may be applied to a system composed of one or more apparatuses, which is based on connection to a network (or communication between apparatuses), for example, cloud computing and the like. That is, the above-described information processing apparatus according to the present embodiment may be realized, for example, as an information processing system that performs processes related to the information processing method according to the present embodiment using a plurality of apparatuses.

(Program According to Present Embodiment)

A program for causing a computer to function as the information processing apparatus according to the present embodiment (e.g., a program for enabling execution of processes related to the information processing method according to the present embodiment) is executed by a processor or the like in the computer, so that user convenience can be improved.

In addition, the program for causing a computer to function as the information processing apparatus according to the present embodiment is executed by a processor or the like in the computer, and thus the aforementioned effects obtained by processes related to the information processing method according to the present embodiment can be achieved.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, although provision of a program for causing a computer to function as the information processing apparatus according to the present embodiment (computer program) has been described above, the present embodiment may further provide a recording medium storing the program.

The aforementioned configuration is an example of the present embodiment and, of course, belongs to the technical scope of the present description.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including a processing unit configured to perform a predetermined process on the basis of first information about a user that is acquired by a first apparatus from around a body of the user, and second information about a user that is acquired by a second apparatus different from the first apparatus.

(2)

The information processing apparatus according to (1), in which the first information is information acquired from the body of the user wearing the first apparatus on the body.

(3)

The information processing apparatus according to (1), in which the first information is information acquired from the body of the user in contact with the first apparatus.

(4)

The information processing apparatus according to (1), in which the first information is one or more of bio-information of a user, information indicating a motion, and information about a behavior history, the second information is one or more of bio-information of a user, information indicating a motion, and information about a behavior history, and the processing unit compares the first information or information based on the first information with the second information corresponding to the first information or information based on the second information.

(5)

The information processing apparatus according to (4), in which the bio-information includes information indicating detection result of a pulse wave.

(6)

The information processing apparatus according to (5), in which the second information is an image captured by a user, and the first information is information indicating a detection result of a pulse wave sensor that detects a pulse wave.

(7)

The information processing apparatus according to any one of (4) to (6), in which the bio-information includes information indicating a myoelectric detection result.

(8)

The information processing apparatus according to (7), in which the second information is an image captured by a user, and the first information is information indicating a detection result of a myoelectric sensor that detects myoelectricity.

(9)

The information processing apparatus according to any one of (1) to (8), in which the processing unit switches the predetermined process on the basis of whether a user corresponding to the first information is identical to a user corresponding to the second information.

(10)

The information processing apparatus according to (9), in which, in the case where the user corresponding to the first information is identical to the user corresponding to the second information, the predetermined process is a process that enables a manipulation specific to the user.

(11)

The information processing apparatus according to (10), in which the predetermined process is a process that enables a manipulation corresponding to the user to be performed.

(12)

The information processing apparatus according to (10), in which the predetermined process is a process that enables a manipulation of a target associated with the user.

(13)

The information processing apparatus according to (10), in which the predetermined process is a process of performing a manipulation of locking or unlocking a target associated with the user.

(14)

The information processing apparatus according to any one of (1) to (13), in which the processing unit acquires third information corresponding to a user who owns the first apparatus on the basis of information indicating a first apparatus acquired from the first apparatus, and performs the predetermined process on the basis of the third information and the second information or information based on the second information.

(15)

The information processing apparatus according to (14), in which the first information or information based on the first information is recorded in association with information indicating the first apparatus, and the processing unit acquires the first information or the information based on the first information that is recorded in association with the information indicating the first apparatus, as the third information.

(16)

An information processing method executed by an information processing apparatus, the information processing method including a step of performing a predetermined process on the basis of first information about a user that is acquired by a first apparatus from around a body of the user, and second information about a user that is acquired by a second apparatus different from the first apparatus.

(17)

A program for causing a computer to execute a step of performing a predetermined process on the basis of first information about a user that is acquired by a first apparatus from around a body of the user, and second information about a user that is acquired by a second apparatus different from the first apparatus.

REFERENCE SIGNS LIST 100 information processing apparatus
102 communication unit
104 control unit
110 processing unit
200 second apparatus
300, 300A, 300B, 300C, 300E, 300F first apparatus

The invention claimed is:

1. An information processing apparatus, comprising:
a memory configured to store instructions; and
at least one processor configured to execute the instructions to:
  acquire first information of a first user from a first apparatus, wherein
    the first apparatus acquires the first information from around a body of the first user, and
    the first apparatus is one of wearable on the body of the first user or in contact with the body of the first user;
  set a threshold time duration that corresponds to a time duration from a time at which the first information is acquired;
  acquire second information of a second user from a second apparatus, wherein
    the second apparatus acquires the second information from a sensor, and
    the second apparatus is different from the first apparatus and the information processing apparatus;
  determine that the second information is acquired from the second apparatus within the threshold time duration;
  compare the first information with the second information based on the determination that the second information is acquired from the second apparatus within the threshold time duration, wherein
    the first information includes information about a behavior history of the first user and at least one of bio-information of the first user or information that indicates a motion of the first user,
    the bio-information of the first user indicates a detection result of a pulse wave sensor, and
    the second information includes information about a behavior history of the second user and at least one of bio-information of the second user or information that indicates a motion of the second user;
  determine, based on the comparison of the first information with the second information, the first user corresponding to the first information is identical to the second user corresponding to the second information;
  acquire third information from the first apparatus, wherein the third information indicates identity of the first apparatus;
  generate fourth information based on the third information, wherein the fourth information corresponds to the first user of the first apparatus;
  compare the fourth information with the second information that is acquired from the second apparatus;
  determine, based on the comparison of the fourth information with the second information, the first user corresponding to the fourth information is identical to the second user corresponding to the second information; and
  execute a process based on the determination that the first user corresponding to the first information is identical to the second user and the determination that the first user corresponding to the fourth information is identical to the second user.

2. The information processing apparatus according to claim 1, wherein
the second information corresponds to an image of the second user, and
the detection result of the pulse wave sensor corresponds to pulse wave that is associated with the first user.

3. The information processing apparatus according to claim 1, wherein the at least one processor is further configured to execute the instructions to switch the process based on the determination that the first user corresponding to the first information is identical to the second user corresponding to the second information and the determination that the first user corresponding to the fourth information is identical to the second user corresponding to second user.

4. The information processing apparatus according to claim 3, wherein the process enables a first manipulation specific to the first user.

5. The information processing apparatus according to claim 4, wherein
the process enables execution of a second manipulation, and
the second manipulation corresponds to the first user.

6. The information processing apparatus according to claim 4, wherein
the process enables a second manipulation of a target, and
the target is associated with the first user.

7. The information processing apparatus according to claim 4, wherein
the process corresponds to a second manipulation of one of locking or unlocking a target, and
the target is associated with the first user.

8. The information processing apparatus according to claim 1, wherein the at least one processor is further configured to execute the instructions to:
  record the first information in association with information indicating the first apparatus; and
  acquire, as the fourth information, the recorded first information.

9. An information processing method, comprising:
in an information processing apparatus:
acquiring first information of a first user from a first apparatus, wherein
the first apparatus acquires the first information from around a body of the first user, and
the first apparatus is one of wearable on the body of the first user or in contact with the body of the first user;
setting a threshold time duration that corresponds to a time duration from a time at which the first information is acquired;
acquiring second information of a second user from a second apparatus, wherein
the second apparatus acquires the second information from a sensor, and
the second apparatus is different from the first apparatus and the information processing apparatus;
determining that the second information is acquired from the second apparatus within the threshold time duration;
comparing the first information with the second information based on the determination that the second information is acquired from the second apparatus within the threshold time duration, wherein
the first information includes information about a behavior history of the first user and at least one of bio-information of the first user or information that indicates a motion of the first user,
the bio-information of the first user indicates a detection result of a pulse wave sensor, and
the second information includes information about a behavior history of the second user and at least one of bio-information of the second user or information that indicates a motion of the second user;
determining, based on the comparison of the first information with the second information, the first user corresponding to the first information is identical to the second user corresponding to the second information;
acquiring third information from the first apparatus, wherein the third information indicates identity of the first apparatus;
generating fourth information based on the third information, wherein the fourth information corresponds to the first user of the first apparatus;
comparing the fourth information with the second information that is acquired from the second apparatus;
determining, based on the comparison of the fourth information with the second information, the first user corresponding to the fourth information is identical to the second user corresponding to the second information; and
executing a process based on the determination that the first user corresponding to the first information is identical to the second user and determination that the first user corresponding to the fourth information is identical to the second user.

10. A non-transitory computer-readable medium having stored thereon computer-executable instructions, which when executed by at least one processor of an information processing apparatus, cause the at least one processor to execute operations, the operations comprising:
acquiring first information of a first user from a first apparatus, wherein
the first apparatus acquires the first information from around a body of the first user, and
the first apparatus is one of wearable on the body of the first user or in contact with the body of the first user;
setting a threshold time duration that corresponds to a time duration from a time at which the first information is acquired;
acquiring second information of a second user from a second apparatus, wherein
the second apparatus acquires the second information from a sensor, and
the second apparatus is different from the first apparatus and the information processing apparatus;
determining that the second information is acquired from the second apparatus within the threshold time duration;
comparing the first information with the second information based on the determination that the second information is acquired from the second apparatus within the threshold time duration, wherein
the first information includes information about a behavior history of the first user and at least one of bio-information of the first user or information that indicates a motion of the first user,
the bio-information of the first user indicates a detection result of a pulse wave sensor, and
the second information includes information about a behavior history of the second user and at least one of bio-information of the second user or information that indicates a motion of the second user;
determining, based on the comparison of the first information with the second information, the first user corresponding to the first information is identical to the second user corresponding to the second information;
acquiring third information from the first apparatus, wherein the third information indicates identity of the first apparatus;
generating fourth information based on the third information, wherein the fourth information corresponds to the first user of the first apparatus;
comparing the fourth information with the second information that is acquired from the second apparatus;
determining, based on the comparison of the fourth information with the second information, the first user corresponding to the fourth information is identical to the second user corresponding to the second information; and
executing a process based on the determination that the first user corresponding to the first information is identical to the second user and the determination that the first user corresponding to the fourth information is identical to the second user.

11. An information processing apparatus, comprising:
a memory configured to store instructions; and
at least one processor configured to execute the instructions to:
acquire first information of a first user from a first apparatus, wherein
the first apparatus acquires the first information from around a body of the first user, and
the first apparatus is one of wearable on the body of the first user or in contact with the body of the first user;
set a threshold time duration that corresponds to a time duration from a time at which the first information is acquired;

acquire second information of a second user from a second apparatus, wherein
  the second apparatus acquires the second information from a sensor, and
  the second apparatus is different from the first apparatus and the information processing apparatus;
determine that the second information is acquired from the second apparatus within the threshold time duration;
compare the first information with the second information based on the determination that the second information is acquired from the second apparatus within the threshold time duration, wherein
  the first information includes information about a behavior history of the first user and at least one of bio-information of the first user or information that indicates a motion of the first user,
  the bio-information of the first user indicates a myoelectric detection result, and
  the second information includes information about a behavior history of the second user and at least one of bio-information of the second user or information that indicates a motion of the second user;
determine, based on the comparison of the first information with the second information, the first user corresponding to the first information is identical to the second user corresponding to the second information;
acquire third information from the first apparatus, wherein the third information indicates identity of the first apparatus;
generate fourth information based on the third information, wherein the fourth information corresponds to the first user of the first apparatus;
compare the fourth information with the second information that is acquired from the second apparatus;
determine, based on the comparison of the fourth information with the second information, the first user corresponding to the fourth information is identical to the second user corresponding to the second information; and
execute a process based on the determination that the first user corresponding to the first information is identical to the second user and the determination that the first user corresponding to the fourth information is identical to the second user.

* * * * *